(12) United States Patent
Zhang et al.

(10) Patent No.: US 7,022,702 B2
(45) Date of Patent: *Apr. 4, 2006

(54) ANTIPROLIFERATIVE 1,2,3-THIADIAZOLE COMPOUNDS

(75) Inventors: Zaihui Zhang, Richmond (CA); Gregory B. Chopiuk, Vancouver (CA); Timothy S. Daynard, Vancouver (CA); Shisen Wang, Coquitlam (CA)

(73) Assignee: QLT Inc., Vancouver (CA)

( * ) Notice: Subject to any disclaimer, the term of this patent is extended or adjusted under 35 U.S.C. 154(b) by 380 days.

This patent is subject to a terminal disclaimer.

(21) Appl. No.: 10/144,203

(22) Filed: May 10, 2002

(65) Prior Publication Data

US 2003/0096848 A1 May 22, 2003

Related U.S. Application Data

(63) Continuation-in-part of application No. 09/545,237, filed on Apr. 7, 2000, now Pat. No. 6,420,400.

(51) Int. Cl.
A61K 31/433 (2006.01)
C07D 285/06 (2006.01)

(52) U.S. Cl. ................... 514/236.2; 514/361; 544/134; 548/127

(58) Field of Classification Search ............... 548/127; 514/361, 236.2, 134
See application file for complete search history.

(56) References Cited

U.S. PATENT DOCUMENTS

| 3,787,434 A | 1/1974 | Volpp et al. ............. 260/306.8 |
| 3,874,873 A | 4/1975 | Volpp et al. .................... 71/90 |
| 4,101,548 A | 7/1978 | Crenshaw et al. .......... 544/284 |
| 4,171,363 A | 10/1979 | Crenshaw et al. .......... 424/251 |
| 5,098,918 A | 3/1992 | Thomas et al. .............. 514/361 |
| 5,674,886 A | 10/1997 | Okada et al. ................ 514/383 |

FOREIGN PATENT DOCUMENTS

WO    WO 96/29871    10/1996

OTHER PUBLICATIONS

Bakulev et al., "Two Directions of Cyclization of α–Diazo–β–Dithioamides. New Rearrangements of 1,2,3–Triazole–4–Carbothiamides," *Tetrahedron* (1989), vol. 45, pp 7329–7340.

Delcommenne et al., "Phosphoinositide–3–OH Kinase–Dependent Regulation of Glycogen Synthase Kinase 3 and Protein Kinase B/AKT by the Integrin–Linked Kinase," *Proceedings of the National Academy of Sciences, USA* (Sep. 1998), vol. 95, pp 11211–11216.

Kandeel et al., "Oxidative Transformation of Pyrazole into Triazole. Novel Syntheses of 4–Cyano–2H–1,2,3–Triazole Derivatives," *Journal of the Chemical Society, Perkins Transaction 1* (1986), pp 1379–1381.

Kandeel et al., "Activated Nitriles in Heterocyclic Synthesis: Reaction of Cyanogen Bromide with Some Functionally Substituted Enamines," *Journal of the Chemical Society, Perkins Transaction 1* (1985), pp 1499–1501.

Kolobov et al., "Reactions of Diazoacetonitrile Derivatives," *Journal of Organic Chemistry of the USSR* (1987), vol. 23, pp 1011–1012.

Mitchell et al., "Inhibitors of Angiogenesis", *Annual Reports in Medicinal Chemistry* (1992), vol. 27, pp. 139–148.

Bakulev et al., "Domino–type Rearrangements in Conjugated 5–(1,2,3–Triazol–4–yl)1,2,3–thiadiazoles", abstract provided from *Chemical Abstracts Database*, Accession No. 1998:55442. See also *Bull. Soc. Chim. Belg.* (1997), vol. 106, pp 643–645.

(Continued)

*Primary Examiner*—Richard L. Raymond
(74) *Attorney, Agent, or Firm*—Seed IP Law Group PLLC

(57) ABSTRACT

Pharmaceutical compositions and compounds are provided. The compounds of the invention have anti-proliferative activity, and may promote apoptosis in cells lacking normal regulation of cell cycle and death. In one embodiment of the invention, formulations of the compounds in combination with a physiologically acceptable carrier are provided. The pharmaceutical formulations are useful in the treatment of hyperproliferative disorders, which disorders include tumor growth, lymphoproliferative diseases, angiogenesis. The compounds of the invention are 1,2,3-thiadiazoles having the structure:

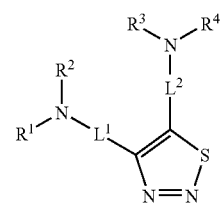

and including stereoisomers, solvates, and pharmaceutically acceptable salts thereof, wherein each of $R^1$, $R^2$, $R^3$ and $R^4$ is independently selected from hydrogen, $R^5R^6$, and $R^7$, $R^5$ is selected from alkyl, heteroalkyl, aryl and heteroaryl; $R^6$ is selected from $(R^5)_n$-alkylene, $(R^5)_n$-heteroalkylene, $(R^5)_n$-arylene and $(R^5)_n$-heteroarylene; $R^7$ is selected from $(R^6)_n$-alkylene, $(R^6)_n$-heteroalkylene, $(R^6)_n$-arylene, and $(R^6)_n$-heteroarylene; and n is selected from 0, 1, 2, 3, 4 and 5, where $R^1$ and $R^2$ may together form a heterocyclic structure including the nitrogen to which they are both attached, and $R^3$ and $R^4$ may together form a heterocyclic structure including the nitrogen to which they are both attached; and each of $L^1$ and $L^2$ is independently selected from -A1-A2-A3- where each of A1, A2, and A3 is independently selected from a direct bond, alkylene, heteroalkylene, arylene and heteroarylene.

12 Claims, No Drawings

OTHER PUBLICATIONS

Bakulev et al., "Synthesis and Study of the Rearrangements of 5–(1,2,3,–Triazol–4–yl)–1,2,3–thiadiazoles", abstract provided from *Chemical Abstracts Database*, Accession No. 1998:454928. See also *Tetrahedron* (1998), vol. 54, pp 8501–8514.

Tarasov et al., "C–Nucleophilic Substitution of 5–Halo–1, 2,3–thiadiazoles As An Approach to Fused Pyridones and Pyranones", abstract provided from *Chemical Abstracts Database*, Accession No. 1997:727791. See also *J. Chem. Res., Synop*. (1997), vol. 11, pp 396–397.

Kuroda et al., "Preparation of Thiadiazole Derivatives as Agricultural Microbicides", abstract provided from *Chemical Abstracts Database*, Accession No. 1996:694344. See also PCT Int. App. WO 96/29871.

Crenshaw et al. "Quinazoline Derivatives", abstract provided from *Chemical Abstracts Database*, Accession No. 1978:597604. See also German Patent No. DE 2807392.

Dankova et al., "Investigation of Malonodithioamide Cyclization Direction As A Method for Study of .alpha.–Diazothioacetamide Reactivity", abstract provided from *Chemical Abstracts Database*, Accession No. 1993:517183. See also *Khim. Geterotsikl. Soedin*. (1992), vol. 8, pp 1106–1112.

Dankova et al., "Methylation of 1,2, 3–Thiadiazole–4–carbothioamides", abstract provided from *Chemical Abstracts Database*, Accession No. 1990:532096. See also *Ivz. Akad. Nauk SSSR, Ser. Khim*. (1990), vol. 4, pp. 938–940.

Lebedev et al., "Mass Spectra of 4,5–Disubstituted 1,2, 3–Thiadiazoles", *Chemistry of Heterocyclic Compounds*. (1988), vol. 24, pp 99–103. (translation).

Morzherin et al., "Study of the Characteristics of Rearrangements of 5–Amino–1,2,3–thiadiazole–4–carbothioamides", *Chemistry of Heterocycles* (1994), vol. 30, pp 483–488.

Morzherin et al., "Nucleophilic Substitution in 1,2,3–Thiadiazoles", *Chemistry of Heterocyclic Compounds* (1994), vol. 30, pp 489–494.

US 7,022,702 B2

ANTIPROLIFERATIVE 1,2,3-THIADIAZOLE COMPOUNDS

CROSS-REFERENCE TO RELATED APPLICATIONS

This application is a Continuation-in-Part of U.S. Utility application Ser. No. 09/545,237, filed Apr. 7, 2000, now issued as U.S. Pat. No. 6,420,400, which is incorporated herein by reference in its entirety.

BACKGROUND OF THE INVENTION

It has become increasingly clear in recent years that cell death is as important to the health of a multicellular organism as cell division: where proliferation exists, so must a means of regulating its cellular progeny. By repeated cell division and differentiation throughout development or tissue repair, surplus or even harmful cells are generated, and they must be removed or killed. In adults, senescent cells are removed and replaced by newly generated cells to maintain homeostasis.

The delicate interplay between growth and cell death in an organism is mirrored in the complex molecular balance that determines whether an individual cell undergoes division; arrests in the cell cycle; or commits to programmed cell death. Signal transduction is the term describing the process of conversion of extracellular signals, such as hormones, growth factors, neurotransmitters, cytokines, and others, to a specific intracellular response such as gene expression, cell division, or apoptosis. This process begins at the cell membrane where an external stimulus initiates a cascade of enzymatic reactions inside the cell that typically include phosphorylation of proteins as mediators of downstream processes which most often end in an event in the cell nucleus. The checks and balances of these signal transduction pathways can be thought of as overlapping networks of interacting molecules that control "go-no go" control points. Since almost all known diseases exhibit dysfunctional aspects in these networks, there has been a great deal of enthusiasm for research that provides targets and therapeutic agents based on signal transduction components linked to disease.

Dysregulation of cell proliferation, or a lack of appropriate cell death, has wide ranging clinical implications. A number of diseases associated with such dysregulation involve hyperproliferation, inflammation, tissue remodelling and repair. Familiar indications in this category include cancers, restenosis, neointimal hyperplasia, angiogenesis, endometriosis, lymphoproliferative disorders, graft-rejection, polyposis, loss of neural function in the case of tissue remodelling, and the like. Such cells may lose the normal regulatory control of cell division, and may also fail to undergo appropriate cell death.

In one example, epithelial cells, endothelial cells, muscle cells, and others undergo apoptosis when they lose contact with extracellular matrix, or bind through an inappropriate integrin. This phenomenon, which has been termed "anoikis" (the Greek word for "homelessness"), prevents shed epithelial cells from colonizing elsewhere, thus protecting against neoplasia, endometriosis, and the like. It is also an important mechanism in the initial cavitation step of embryonic development, in mammary gland involution, and has been exploited to prevent tumor angiogenesis. Epithelial cells may become resistant to anoikis through overactivation of integrin signaling. Anoikis resistance can also arise from the loss of apoptotic signaling, for example, by overexpression of Bcl-2 or inhibition of caspase activity.

An aspect of hyperproliferation that is often linked to tumor growth is angiogenesis. The growth of new blood vessels is essential for the later stages of solid tumor growth. Angiogenesis is caused by the migration and proliferation of the endothelial cells that form blood vessels.

In another example, a major group of systemic autoimmune diseases is associated with abnormal lymphoproliferation, as a result of defects in the termination of lymphocyte activation and growth. Often such diseases are associated with inflammation, for example with rheumatoid arthritis, insulin dependent diabetes mellitus, multiple sclerosis, systemic lupus erythematosus, and the like. Recent progress has been made in understanding the causes and consequences of these abnormalities. At the molecular level, multiple defects may occur, which result in a failure to set up a functional apoptotic machinery.

The development of compounds that inhibit hyperproliferative diseases, particularly where undesirable cells are selectively targeted, is of great medical and commercial interest.

Relevant literature:

Triazolylated tertiary amine compounds are provided in U.S. Pat. No. 5,674,886. U.S. Pat. Nos. 4,101,548 and 4,171,363 disclose quinazoline compounds, and in particular 2-piperazinyl-6,7-dimethoxyquinazolines compounds that include a 1,2,3-thiadiazole terminal group. U.S. Pat. Nos. 3,787,434 and 3,874,873 disclose herbicidal compounds and compositions that include 1,2,3-thiadiazole-5-yl ureas.

Chemical compounds are disclosed in Tarasov et al., Khim. Geterotsiki. Soedin. 8:1124–1127, 1996; Morzherin, Tarasov and Bakulev, Khim. Geterotsikl Soedin. 4:554–559, 1994; Morzherin, Bakulev, Dankova and Mokrushin, Khim. Geterotsikl Soedin 4:548–553, 1994, Shafran, Bakulev, Shevirin, and Kolobov, Khim. Geterotsikl. Soedin. 6:840-6, 1993; Dankova, Bakulev, and Morzherin, Khim. Geterotsikl. Soedin. 8:1106–1112, 1992; Bakulev, Lebedev, Dankova, Mokrushin, and Petrosyan, Tetrahedron 45(23):7329–7340, 1989; Kankova, Bakulev, Kolobov, Andosova, and Mokrushin, Khim. Geterotsikl, Soedin. 6:827–829, 1989; Dankova, Bakulev, Kolobov, Shishkina, Yasman, and Lebedev, Khim. Geterotsikl. Soedin 9:1269–1273, 1988; Bakulev, Kolobov, Grishakov, and Mokrushin, Izv. Akad. Nauk SSR, Ser. Khim. 1:193–195, 1988; Kolobov, Bakulev, Mokrushin, and Lebedev, Khim. Geterotsikl. Soedin 11:1503–1508, 1987; Bakulev, Dankova, Mokrushin, Sidorov, and Lebedev, Khim. Geterotsikl. Soedin. 6:845–849, 1987; Kolobov, Bakulev, and Mokrushin, Zh. Org. Khim. 23(5):1120–1122, 1987; Lebedev, Shevchenko, Kazaryan, Bakulev, Shafran, Kolobov, and Prosyan, Khim. Geterotsikl. Soedin. 5:681–689, 1987; Shafran, Bakulev, Mokrushin, and Validuda, Khim. Geterotsikl. Soedin. 5:691–696, 1986; Dankova, Bakulev, Mokrushin, and Shafran, Khim. Geterotsiki. Soedin, 10:1429–1430, 1985; and Shafran, Bakulev, Mokrushin, and Pushkareva, Khim. Geterotsikl. Soedin. 12:1696–1697, 1982; and Gewald and Hain, J. Prakt. Chem. 317(2):329–336, 1975.

The regulation of integrin linked kinase by phosphatidylinositol (3,4,5) trisphosphate is described by Delcommenne et al. (1998) Proc Natl Acad Sci 95:11211-6. Activated nitriles in heterocyclic synthesis are discussed in Kandeel et al. (1985) J. Chem. Soc. Perkin. Trans 1499. Oxidative transformation of pyrazole into triazole is discussed in Kandeel et al. (1986) J. Chem. Soc. Perkin. Trans 1379.

SUMMARY OF THE INVENTION

Pharmaceutical compositions and compounds are provided. The compounds of the invention are 1,2,3thiadiazole compounds. In one embodiment of the invention, formulations of the compounds in combination with a physiologically acceptable carrier are provided. The pharmaceutical formulations are useful in the treatment of disorders associated with hyperproliferation and tissue remodelling or repair. The compounds are also active in the inhibition of specific protein kinases.

DETAILED DESCRIPTION OF EMBODIMENTS OF THE INVENTION

The present invention provides novel compounds, compositions and methods as set forth within this specification. In general, all technical and scientific terms used herein have the same meaning as commonly understood to one of ordinary skill in the art to which this invention belongs, unless clearly indicated otherwise. For clarification, listed below are definitions for certain terms used herein to describe the present invention. These definitions apply to the terms as they are used throughout this specification, unless otherwise clearly indicated.

DEFINITION OF TERMS

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

"Acyl" is a specie of heteroalkyl wherein a terminal carbon of the heteroalkyl group is in the form of a carbonyl group, i.e., (alkyl or heteroalkyl)—C═O, where examples include acetyl ($CH_3$—(C═O)—).

"Acyloxy" refers to a heteroalkylene group of the formula —C(═O)—O— bonded to "X" so as to form —C(═O)—O—X wherein X may be any of alkyl, aryl, heteroalkyl, or heteroaryl.

"Alkenyl" is a specie of alkyl group, where an alkenyl group has at least one carbon—carbon double bond.

"Alkenylene" is a specie of alkylene group where the alkylene group has at least one double bond.

"Alkyl" is a monovalent, saturated or unsaturated, straight, branched or cyclic, aliphatic (i.e., not aromatic) hydrocarbon group. In various embodiments, the alkyl group has 1–20 carbon atoms, i.e., is a C1–C20 (or $C_1$–$C_{20}$) group, or is a C1–C18 group, a C1–C12 group, a C1–C6 group, or a C1–C4 group. Independently, in various embodiments, the alkyl group: has zero branches (i.e., is a straight chain), one branch, two branches, or more than two branches; is saturated; is unsaturated (where an unsaturated alkyl group may have one double bond, two double bonds, more than two double bonds, and/or one triple bond, two triple bonds, or more than three triple bonds); is, or includes, a cyclic structure; is acyclic. Exemplary alkyl groups include $C_1$, alkyl (i.e., —$CH_3$ (methyl)), $C_2$ alkyl (i.e., —$CH_2CH_3$ (ethyl), —CH═$CH_2$ (ethenyl) and —C≡CH (ethynyl)) and $C_3$ alkyl (i.e., —$CH_2CH_2CH_3$ (n-propyl), —CH$(CH_3)_2$ (i-propyl), —CH═CH—$CH_3$ (1-propenyl), —C≡C—$CH_3$ (1-propynyl), —$CH_2$—CH═$CH_2$ (2-propenyl), —$CH_2$—C≡CH (2-propynyl), —C$(CH_3)$═$CH_2$ (1-methylethenyl), and —CH$(CH_2)_2$ (cyclopropyl)).

"Alkylene" is a polyvalent, saturated or unsaturated, straight, branched or cyclic, aliphatic (i.e., not aromatic) hydrocarbon group. In various embodiments, the alkylene group has 1–20 carbon atoms, i.e., is a C1–C20 group, or is a C1–C18 group, a C1–C12 group, a C1–C6 group, or a C1–C4 group. Independently, in various embodiments, the alkylene group: has zero branches (i.e., is a straight chain), one branch, two branches, or more than two branches; is saturated; is unsaturated (where an unsaturated alkylene group may have one double bond, two double bonds, more than two double bonds, and/or one triple bond, two triple bonds, or more than three triple bonds); is or contains a cyclic group; is acyclic; is divalent, i.e., has two open sites that each bond to a non-alkylene group; is trivalent, i.e., has three open sites that each bond to a non-alkylene group; has more than three open sites. Exemplary alkylene groups include $C_1$alkylene (i.e., —$CH_2$—) and $C_2$alkylene (i.e., —$CH_2CH_2$—, —CH═CH—, —C≡C—, —C(═$CH_2$)—, and —CH($CH_3$)—).

"Aralkenyl" is another name for arylalkenylene, wherein at least one of the open bonding sites of an alkenylene group is bonded to an aryl group.

"Aralkyl" is another name for arylalkylene, wherein at least one of the open bonding sites of an alkylene group is bonded to an aryl group, where benzyl is an example.

"Aryl" is a monovalent, aromatic, hydrocarbon, ring system. The ring system may be monocyclic or fused polycyclic (e.g., bicyclic, tricyclic, etc.). In various embodiments, the monocyclic aryl ring is C5–C10, or C5–C7, or C5–C6, where these carbon numbers refer to the number of carbon atoms that form the ring system. A C6 ring system, i.e., a phenyl ring, is a preferred aryl group. In various embodiments, the polycyclic ring is a bicyclic aryl group, where preferred bicyclic aryl groups are C8–C12, or C9–C10. A naphthyl ring, which has 10 carbon atoms, is a preferred polycyclic aryl group.

"Arylene" is a polyvalent, aromatic hydrocarbon, ring system. The ring system may be monocyclic or fused polycyclic (e.g., bicyclic, tricyclic, etc.). In various embodiments, the monocyclic arylene group is C5–C10, or C5–C7, or C5–C6, where these carbon numbers refer to the number of carbon atoms that form the ring system. A C6 ring system, i.e., a phenylene ring, is a preferred aryl group. In various embodiments, the polycyclic ring is a bicyclic arylene group, where preferred bicyclic arylene groups are C8–C12, or C9–C10. A naphthylene ring, which has 10 carbon atoms, is a preferred polycyclic aryl group. The arylene group may be divalent, i.e., it has two open sites that each bond to another group; or trivalent, i.e., it has three open sites that each bond to another group; or it may have more than three open sites.

"Cycloalkenyl" is a specie of alkyl group where a cycloalkenyl group is a cyclic hydrocarbon group with at least one double bond.

"Cycloalkenylene" is a specie of alkylene group which is a cyclic hydrocarbon with at least one double bond and with at least two bonding sites.

"Cycloalkyl" is a specie of alkyl group, where a cycloalkyl is a cyclic hydrocarbon group.

"Cycloalkylalkylene" is a species of alkyl group wherein at least one open bonding site of an alkylene group is joined to a cycloalkyl group.

"Cycloalkylene" is a specie of alkylene group which is a cyclic hydrocarbon group with at least two open bonding sites.

"Cycloalkylenealkylene" is a specie of alkylene group wherein a cycloalkylene group is bonded to a non-cyclic alkylene group, and each of the cycloalkylene and non-cyclic alkylene group have at least one open bonding site.

Haloalkyl is a specie of heteroalkyl wherein at least one carbon of an alkyl group is bonded to at least one halogen.

"Halogen" refers to fluorine, chlorine, bromine and iodide. Fluorine and chlorine are preferred halogens in compounds and compositions of the present invention.

Heteroalkylenearyl is a heteroalkylene group with at least one of its open bonding sites joined to an aryl group, where benzoyl (—C(=O)—Ph) is an example.

"Heteroalkyl" is an alkyl group (as defined herein) wherein at least one of the carbon atoms is replaced with a heteroatom. Preferred heteroatoms are nitrogen, oxygen, sulfur, and halogen. A heteroatom may, but typically does not, have the same number of valence sites as carbon. Accordingly, when a carbon is replaced with a heteroatom, the number of hydrogens bonded to the heteroatom may need to be increased or decreased to match the number of valence sites of the heteroatom. For instance, if carbon (valence of four) is replaced with nitrogen (valence of three), then one of the hydrogens formerly attached to the replaced carbon must be deleted. Likewise, if carbon is replaced with halogen (valence of one), then three (i.e., all) of the hydrogens formerly bonded to the replaced carbon must be deleted.

"Heteroalkylene" is an alkylene group (as defined herein) wherein at least one of the carbon atoms is replaced with a heteroatom. Preferred heteroatoms are nitrogen, oxygen, sulfur, and halogen. A heteroatom may, but typically does not, have the same number of valence sites as carbon. Accordingly, when a carbon is replaced with a heteroatom, the number of hydrogens bonded to the heteroatom may need to be increased or decreased to match the number of valence sites of the heteroatom, as explained elsewhere herein.

"Heteroaralkenyl" is another name for heteroarylalkenylene, wherein at least one of the open bonding sites of an alkenylene group is bonded to a heteroaryl group.

"Heteroaralkyl" is another name for heteroarylalkylene, wherein at least one of the open bonding sites of an alkylene group is bonded to a heteroalkyl group.

"Heteroaryl" is a monovalent aromatic ring system containing carbon and at least one heteroatom in the ring. The heteroaryl group may, in various embodiments, have one heteroatom, or 1–2 heteroatoms, or 1–3 heteroatoms, or 1–4 heteroatoms in the ring. Heteroaryl rings may be monocyclic or polycyclic, where the polycyclic ring may contain fused, spiro or bridged ring junctions. In one embodiment, the heteroaryl is selected from monocyclic and bicyclic. Monocyclic heteroaryl rings may contain from about 5 to about 10 member atoms (carbon and heteroatoms), preferably from 5–7, and most preferably from 5–6 member atoms in the ring. Bicyclic heteroaryl rings may contain from about 8–12 member atoms, or 9–10 member atoms in the ring. The heteroaryl ring may be unsubstituted or substituted. In one embodiment, the heteroaryl ring is unsubstituted. In another embodiment, the heteroaryl ring is substituted. Exemplary heteroaryl groups include benzofuran, benzothiophene, furan, imidazole, indole, isothiazole, oxazole, piperazine, pyrazine, pyrazole, pyridazine, pyridine, pyrimidine, pyrrole, quinoline, thiazole and thiophene.

"Heteroarylene" is a polyvalent aromatic ring system containing carbon and at least one heteroatom in the ring. In other words, a heteroarylene group is a heteroaryl group that has more than one open site for bonding to other groups. The heteroarylene group may, in various embodiments, have one heteroatom, or 1–2 heteroatoms, or 1–3 heteroatoms, or 1–4 heteroatoms in the ring. Heteroarylene rings may be monocyclic or polycyclic, where the polycyclic ring may contain fused, spiro or bridged ring junctions. In one embodiment, the heteroaryl is selected from monocyclic and bicyclic. Monocyclic heteroarylene rings may contain from about 5 to about 10 member atoms (carbon and heteroatoms), preferably from 5–7, and most preferably from 5–6 member atoms in the ring. Bicyclic heteroarylene rings may contain from about 8–12 member atoms, or 9–10 member atoms in the ring.

"Heteroatom" is a halogen, nitrogen, oxygen, silicon or sulfur atom. Groups containing more than one heteroatom may contain different heteroatoms.

"Pharmaceutically acceptable salt" and "salts thereof" in the compounds of the present invention refers to acid addition salts and base addition salts.

Acid addition salts refer to those salts formed from compounds of the present invention and inorganic acids such as hydrochloric acid, hydrobromic acid, sulfuric acid, nitric acid, phosphoric acid and the like, and/or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Base addition salts refer to those salts formed from compounds of the present invention and inorganic bases such as sodium, potassium, lithium, ammonium, calcium, magnesium, iron, zinc, copper, manganese, aluminum salts and the like. Suitable salts include the ammonium, potassium, sodium, calcium and magnesium salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, and the like.

COMPOUNDS

In one aspect the present invention provides 1,2,3-thiadiazole compounds, where such compounds include the heterocyclic ring system of formula (A). Formula (A) also indicates the numbering system used to uniquely identify each atom of the ring.

(A)

Accordingly, the present invention provides compounds that include a five-membered ring, with unsaturation between the two ring nitrogens and the two ring carbons, i.e., unsaturation between the atoms at positions 2 and 3, and between 4 and 5.

The present inventors have discovered that certain derivatives of the 1,2,3-thiadiazole ring system have desirable bioactivity that render them useful in pharmaceutical compositions and methods of treatment, etc. More specifically, in one aspect, the present invention provides compounds of formula (1)

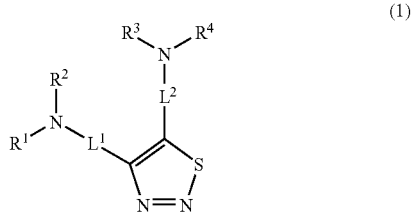

and stereoisomers, solvates, and pharmaceutically acceptable salts thereof.

In formula (1), each of $R^1$, $R^2$, $R^3$ and $R^4$ is independently selected from hydrogen, $R^5$, $R^6$, and $R^7$. $R^5$ is selected from alkyl, heteroalkyl, aryl and heteroaryl; $R^6$ is selected from $(R^{55})_n$-alkylene, $(R^5)_n$-heteroalkylene, $(R^5)_n$-arylene and $(R^5)_n$-heteroarylene; $R^7$ is selected from $(R^6)_n$-alkylene, $(R^6)$n-heteroalkylene, $(R^6)_n$-arylene, and $(R^6)_n$-heteroarylene; and n is selected from 0, 1, 2, 3, 4 and 5. In formula (1), $R^1$ and $R^2$ may together form a heterocyclic structure including the nitrogen to which they are both attached, and $R^3$ and $R^4$ may together form a heterocyclic structure including the nitrogen to which they are both attached. Also in formula (1), each of $L^1$ and $L^2$ is independently selected from —A1-A2-A3— where each of A1, A2, and A3 is independently selected from a direct bond, alkylene, heteroalkylene, arylene and heteroarylene.

In one aspect, each of $R^1$, $R^2$, $R^3$ and $R^4$ is a C1–C20 group selected from alkyl (e.g., alkyl and cycloalkyl, such as ethyl, propyl, butyl, hexyl, cyclohexyl, and adamantyl), heteroalkyl (e.g., $CH_3CH_2$—O-carbonyl, furanyl-carbonyl, hexyl-carbonyl, and adamantyl-carbonyl), aryl (e.g., phenyl and naphthyl), and heteroaryl (e.g., pyridyl). In another aspect, each of $R^1$, $R^2$, $R^3$ and $R^4$ is additionally, or alternatively, selected from alkylarylene (e.g., methylphenyl, ethylphenyl and cyclohexylphenyl), heteroalkylarylene (e.g., bromophenyl and methoxyphenyl), alkytheteroarylene (e.g., methylpyridyl), heteroalkylheteroarylene (e.g., methoxypyridyl), arylalkylene (e.g., phenylmethylene (i.e., benzyl) and phenylethylene), heteroarylalkylene (e.g., pyridyl-$CH_2$—), arylheteroalkylene (e.g., phenylcarbonyl (i.e., benzoyl), naphthylcarbonyl, and phenyl-$CH_2CH_2$-carbonyl), heteroarylheteroalkylene (e.g., pyridyl-carbonyl), arylarylene (e.g., biphenyl), heteroarylarylene (e.g., pyridyl-phenyl), heteroarylheteroarylene (e.g., pyridyl-pyridyl), and arylheteroarylene (e.g., phenyl-pyridyl).

In one aspect, $R^1$, $R^2$, $R^3$, and $R^4$ are each independently selected from hydrogen, alkyl, heteroalkyl, aryl, heteroaryl, heterocycloalkyl, cycloalkylalkylene, arylalkylene, heteroarylalkylene, heterocycloalkylalkylene; alkyl-O, heteroalkyl-O, aryl-O, heteroaryl-O, cycloalkyl-O, heterocycloalkyl-O, cycloalkylalkylene-O, arylalkylene-O, heteroarylalkylene-O, heterocycloalkylalkylene-O; alkyl-CO, heteroalkyl-CO, aryl-CO, heteroaryl-CO, cycloalkyl-CO, heterocycloalkyl-CO, cycloalkylalkylene-CO, arylalkylene-CO, heteroarylalkylene-CO, heterocycloalkylalkylene-CO; alkyl-CONH, heteroalkyl-CONH, aryl-CONH, heteroaryl-CONH, cycloalkyl-CONH, heterocycloalkyl-CONH, cycloalkylalkylene-CONH, arylalkylene-CONH, heteroarylalkylene-CONH, heterocycloalkylalkylene-CONH; alkyl-OCO, heteroalkyl-OCO, aryl-OCO, heteroaryl-OCO, cycloalkyl-OCO, heterocycloalkyl-OCO, cycloalkylalkylene-OCO, arylalkylene-OCO, heteroarylalkylene-OCO, heterocycloalkylalkylene-OCO; alkyl-$SO_2$, heteroalkyl-$SO_2$, aryl-$SO_2$, heteroaryl-$SO_2$, cycloalkyl-$SO_2$, heterocycloalkyl-$SO_2$, cycloalkylalkylene-$SO_2$, arylalkylene-$SO_2$, heteroarylalkylene-$SO_2$, and heterocycloalkylalkylene-$SO_2$.

In one aspect, $R^1$, $R^2$, $R^3$, and $R^4$ are each independently selected from hydrogen, alkyl, heteroalkyl, aryl, heteroaryl, heterocycloalkyl, heteroalkyl.

In one aspect, $R^1$ and $R^2$ are each hydrogen.

In one aspect, $R^3$ is hydrogen or alkyl. In another aspect, $R^3$ is hydrogen.

In one aspect, $R^4$ is $R^6$, where $R^6$ is selected from $(R^5)_n$-alkylene, $(R^5)_n$-heteroalkylene, $(R^5)_n$-arylene and $(R^5)_n$-heteroarylene, and $R^5$ is selected from alkyl, heteroalkyl, aryl and heteroaryl, and n is selected from 0, 1, 2, 3, 4 and 5. In another aspect, $R^4$ is $R^6$, where $R^6$ is selected from $(R^5)_n$-arylene and $(R^5)_n$-heteroarylene, and $R^5$ is selected from alkyl and heteroalkyl, and n is selected from 0, 1, 2, 3, 4 and 5. In another aspect, $R^4$ is $R^6$, where $R^6$ is selected from $(R^5)_n$-arylene and $R^5$ is selected from alkyl and heteroalkyl, and n is selected from 0, 1, 2, 3, 4 and 5.

In one aspect, the present invention provides compounds of formula (1), wherein each of $L^1$ and $L^2$ is independently selected from —A1-A2-A3— such that each of A1 and A2 is a direct bond, and A3 is selected from a direct bond, alkylene, heteroalkylene, arylene and heteroarylene. In another aspect, the present invention provides compounds of formula (1), wherein each of $L^1$ and $L^2$ is independently selected from —A1-A2-A3— such that each of A1 and A2 is a direct bond, and A3 is selected from a direct bond, alkyl, and heteroalkyl. In another aspect, the present invention provides compounds of formula (1), wherein each of $L^1$ and $L^2$ is independently selected from —A1-A2-A3— such that each of A1, A2, and A3 is a direct bond. In another aspect, the present invention provides compounds that exclude carbonyl or thiocarbonyl as L1 or L2. In another aspect, L1 is carbonyl or thiocarbonyl while L2 is a direct bond. In another aspect, L1 is a direct bond while L2 is selected from carbonyl and thiocarbonyl.

In various aspects, the compounds of formula (1) exclude L1═direct bond, and/or L2═direct bond, and/or $R^1$═H, and/or $R^2$═carboxamide (i.e., $H_2N$—(C═O)—), and/or $R^3$═H, and/or $R^4$═phenyl (i.e., $C_6H_5$).

Certain compounds encompassed by formula (1) have been described in the chemical literature, where these compounds were, for example, used as intermediates in various synthetic schemes, and/or studied for their chemical or physical properties, but were not recognized or reported to have any biological activity. Specific literature citations of this type include: Tarasov et al., Khim. Geterotsikl. Soedin. 8:1124–1127, 1996; Morzherin, Tarasov and Bakulev, Khim. Geterotsikl Soedin. 4:554–559, 1994; Morzherin, Bakulev, Dankova and Mokrushin, Khim. Geterotsikl Soedin 4:548–553, 1994; Shafran, Bakulev, Shevirin, and Kolobov, Khim. Geterotsikl Soedin. 6:840-6, 1993; Dankova, Bakulev, and Morzherin, Khim. Geterotsiki. Soedin. 8:1106–1112, 1992; Bakulev, Lebedev, Dankova, Mokrushin, and Petrosyan, Tetrahedron 45(23):7329–7340, 1989; Kankova, Bakulev, Kolobov, Andosova, and Mokrushin, Khim. Geterotsikl, Soedin. 6:827–829, 1989; Dankova, Bakulev, Kolobov, Shishkina, Yasman, and Lebedev, Khim. Geterotsikl. Soedin 9:1269–1273, 1988; Bakulev, Kolobov, Grishakov, and Mokrushin, Izv. Akad. Nauk SSR, Ser. Khim. 1:193–195, 1988; Kolobov, Bakulev, Mokrushin, and Lebedev, Khim. Geterotsikl. Soedin 11:1503–1508, 1987; Bakulev, Dankova, Mokrushin, Sidorov, and Lebedev, Khim. Geterotsikl. Soedin. 6:845–849, 1987; Kolobov, Bakulev, and Mokrushin, Zh. Org. Khim. 23(5):1120–1122, 1987; Lebedev, Shevchenko, Kazaryan, Bakulev, Shafran, Kolobov, and Prosyan, Khim. Geterotsikl. Soedin. 5:681–689, 1987; Shafran, Bakulev, Mokrushin, and Validuda, Khim. Geterotsikl. Soedin. 5:691–696, 1986; Dankova, Bakulev, Mokrushin, and Shafran, Khim. Geterotsikl. Soedin, 10:1429–1430, 1985; and Shafran, Bakulev, Mokrushin, and Pushkareva, Khim. Geterotsikl. Soedin. 12:1696–1697, 1982; and Gewald and Hain, J. Prakt. Chem. 317(2):329–336, 1975.

To the extent a compound of formula (1) is described, and the preparation thereof is enabled, in one or more of these scientific publications, then in one aspect of the present invention such a compound is excluded from the scope of compounds encompassed by formula (1).

However, in another aspect, the present invention provides an isolated compound of formula (1). That is, a compound of formula (1) that is not substantially contaminated with, or otherwise in contact with any other compound. Accordingly, the present invention provides compound of formula (1) in substantially pure form, i.e., in a purity of greater than about 95% by weight, preferably greater than about 98%, and more preferably greater than about 99% by weight. In one aspect, the impurity in contact with a compound of formula (1) is an organic chemical, e.g., an organic solvent. In another aspect, the impurity in contact with a compound of formula (1) is another compound of formula (1). Thus, in one aspect, the present invention provides a compound of formula (1) that is pure in that it is not in contact with another compound of formula (1).

In a related aspect, the present invention provides a compound of formula (1) in the form of an isolated stereoisomer, where the isolated stereoisomer preferably has greater biological efficacy than other stereoisomeric forms of the compound. Thus, in one aspect, the present invention provides an isolated stereoisomer that is in contact with other stereoisomeric forms to a minimal extent, such that the molar ratio of isolated stereosiomer to other isomeric forms is greater than 95:5, preferably greater than 98:2, and still more preferably 99:1.

In another aspect, the present invention provides a compound of formula (1) in the form of a pharmaceutically acceptable salt.

Particularly where the scientific literature has employed a compound of formula (1) merely as an intermediate in a synthetic procedure, or in purely scientific study, this literature may fail to provide the compound in the form that is desirably employed in preparing a pharmaceutical composition. Thus, in various aspects, the present invention provides compounds of formula (1) in a desirably high purity, or at least purified away from undesirable chemicals, and/or in the form of a pharmaceutically acceptable salt that is desirably employed in preparing a pharmaceutical composition according to the present invention.

U.S. Pat. Nos. 4,101,548 and 4,171,363 disclose quinazoline compounds, and in particular 2-piperazinyl-6,7-dimethoxyquinazolines compounds that include a 1,2,3-thiadiazole terminal group, as well as precursors thereto, as shown in Formula (II), where $M^1$ is hydrogen, lower alkyl, $NH_2$ or $NHCO_2M_2$ in which $M_2$ is lower alkyl. These compounds are disclosed as having antihypertensive properties.

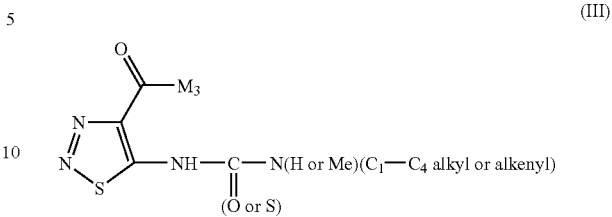

(II)

In one aspect, the present invention excludes compounds of formula (II) from the scope of compounds encompassed by formula (1) of the present invention. In another aspect, the present invention excludes 1,2,3-thiadiazole compounds used as precursors to compounds of formula (II) as set forth in U.S. Pat. Nos. 4,171,363 and 4,171,363.

U.S. Pat. Nos. 3,787,434 and 3,874,873 disclose herbicidal compounds and compositions that include 1,2,3thiadiazole-5-yl ureas of formula (III), where $M_3$ is selected from oxygen- and nitrogen-containing groups as defined in these patents.

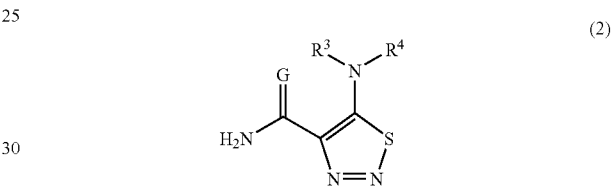

(III)

In one aspect, the present invention excludes compounds of formula (III) from the scope of compounds encompassed by formula (1) of the present invention. In another aspect, the present invention excludes 1,2,3-thiadiazole compounds used as precursors to compounds of formula (III) as set forth in U.S. Pat. Nos. 3,787,434 and 3,874,873.

In one aspect the present invention provides compounds of formula (1) wherein $L^1$ is selected from C=O and C=S, and each of $R^1$ and $R^2$ is hydrogen. In one aspect thereof, $L^2$ is a direct bond, so that the present invention provides compounds of formula (2)

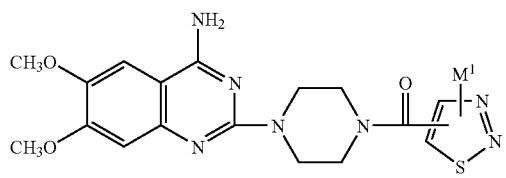

(2)

and stereoisomers, solvates, and pharmaceutically acceptable salts thereof, wherein $R^3$ and $R^4$ are each independently selected from hydrogen, $R^5$, $R^6$, and $R^7$. $R^5$ is selected from alkyl, heteroalkyl, aryl and heteroaryl; $R^6$ is selected from $(R^5)_n$-alkylene, $(R^5)_n$-heteroalkylene, $(R^5)_n$-arylene and $(R^5)_n$-heteroarylene; $R^7$ is selected from $(R^6)_n$-alkylene, $(R^6)_n$-heteroalkylene, $(R^6)_n$-arylene, and $(R^6)_n$-heteroarylene; and n is selected from 0, 1, 2, 3, 4 and 5. In formula (2), $R^3$ and $R^4$ may together form a heterocyclic structure including the nitrogen to which they are both attached.

In one aspect, the present invention provides compounds of formulae (1) and (2) wherein $R^3$ and $R^4$ are independently selected from hydrogen, alkyl (e.g., C1–C20 alkyl and cycloalkyl, such as ethyl, propyl, butyl, hexyl, cyclohexyl, and adamantyl), heteroalkyl (e.g., $CH_3CH_2$—O-carbonyl, furanyl-carbonyl, hexyl-carbonyl, and adamantyl-carbonyl), aryl (e.g., phenyl and naphthyl), heteroaryl (e.g., pyridyl), alkylarylene (e.g., methylphenyl, ethylphenyl and cyclohexylphenyl), heteroalkylarylene (e.g., bromophenyl and methoxyphenyl), alkylheteroarylene (e.g., methylpyridyl), heteroalkylheteroarylene (e.g., methoxypyridyl), arylalkylene (e.g., phenylmethylene (i.e., benzyl) and phenylethylene), heteroarylalkylene (e.g., pyridyl-$CH_2$—), arylheteroalkylene (e.g., phenylcarbonyl (i.e., benzoyl), naphthylcarbonyl, and phenyl-$CH_2CH_2$-carbonyl), heteroarylheteroalkylene (e.g., pyridyl-carbonyl), arylarylene (e.g., biphenyl), heteroarylarylene (e.g., pyridyl-phenyl), heteroarylheteroarylene (e.g., pyridyl-pyridyl), arylheteroarylene (e.g., phenyl-pyridyl), alkylarylenehetroalkylene (e.g., t-butylphenyl-carbonyl), alkylarylenealkylene (e.g., 2-methylbenzyl, 4-methylbenzyl, 4-ethylbenzyl), heteroalkylaryleneheteroalkylene (e.g., methoxyphenyl-carbonyl-, nitrophenyl-carbonyl), and heteroalkylarylenealkylene (e.g., 4-hydroxybenzyl).

In one aspect, the present invention provides compounds of formulae (1) and (2) wherein $R^3$ is H.

In one aspect, the present invention provides compounds of formulae (1) and (2) wherein $R^3$ and $R^4$ are selected from hydrogen and hydrocarbon groups.

In one aspect, the present invention provides compounds of formulae (1) and (2) wherein $R^4$ is phenyl or substituted phenyl. In one aspect thereof, the present invention provides compounds of formula (3),

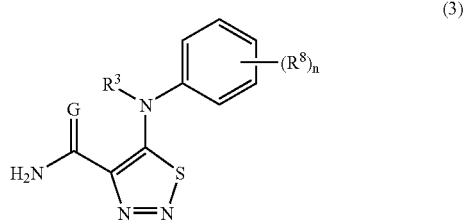

(3)

and stereoisomers, solvates, and pharmaceutically acceptable salts thereof, wherein, independently at each occurrence, G is selected from oxygen and sulfur;

$R^3$ and $R^8$ are selected from hydrogen $R^5$, $R^6$, and $R^7$, where $R^5$ is selected from alkyl, heteroalkyl, aryl and heteroaryl; $R^6$ is selected from $(R^5)_n$-alkylene, $(R^5)_n$-heteroalkylene, $(R^5)_n$-arylene and $(R^5)_n$-heteroarylene; $R^7$ is selected from $(R^6)_n$-alkylene, $(R^6)_n$-heteroalkylene, $(R^6)_n$-arylene, and $(R^6)_n$-heteroarylene; and n is selected from 0, 1, 2, 3, 4 and 5.

In one aspect, the present invention provides compounds of formula (3) wherein $R^3$ is hydrogen, alkyl, or heteroalkyl. In another aspect, the present invention provides compounds of formula (3) wherein $R^3$ is hydrogen or alkyl. In another aspect, the present invention provides compounds of formula (3) wherein $R^3$ is hydrogen.

In one aspect, the present invention provides compounds of formula (3) wherein $R^8$ is $R^5$; $R^5$ is selected from alkyl, heteroalkyl, aryl and heteroaryl; and n is selected from 0, 1, 2, 3, 4 and 5. In one aspect, the present invention provides compounds of formula (3) wherein $R^8$ is $R^5$, and $R^5$ is selected from alkyl and heteroalkyl, and n is selected from 1, 2, 3, 4 and 5.

In one aspect, the present invention provides compounds of formula (4)

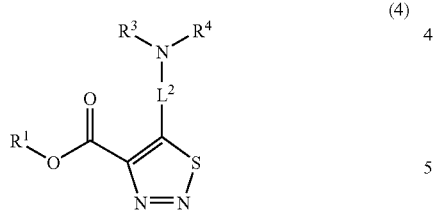

(4)

In formula (4), each of $R^1$, $R^3$ and $R^4$ is independently selected from hydrogen, $R^5$, $R^6$, and $R^7$. $R^5$ is selected from alkyl, heteroalkyl, aryl and heteroaryl; $R^6$ is selected from $(R^5)_n$-alkylene, $(R^5)_n$-heteroalkylene, $(R^5)_n$-arylene and $(R^5)_n$-heteroarylene; $R^7$ is selected from $(R^6)_n$-alkylene, $(R^6)_n$-heteroalkylene, $(R^6)_n$-arylene, and $(R^6)_n$-heteroarylene; and n is selected from 0, 1, 2, 3, 4 and 5. In formula (1), $R^3$ and $R^4$ may together form a heterocyclic structure including the nitrogen to which they are both attached. Also in formula (4), $L^2$ is —A1-A2-A3— where each of A1, A2, and A3 is independently selected from a direct bond, alkylene, heteroalkylene, arylene and heteroarylene.

In various aspects, the present invention provides compounds of formula (4) wherein $R^1$ is an alkyl group, and/or $L^2$ is a direct bond, and/or $R^3$ is hydrogen, and/or $R^4$ is a hydrocarbon group.

SYNTHETIC METHODS

In general, the following three methods and their variations as reported in the literature may be used to prepare 1,2,3-thiadiazole compounds of the present invention. The method of Pechmann and Nold (Ber. 29:2588, 1896) is one of the earliest reported methods to synthesize 1,2,3-thiadiazoles. This method utilizes the reaction of diazomethane and phenyl isothiocyanate (or more broadly, thiocarbonyl compounds) and may be utilized to prepare 5-amine substituted 1,2,3-thiadiazoles and 4,5-disubstituted 1,2,3-thiadiazoles. The method of Wolff (Ann. Chemie, 325:129, 1902) is another long-standing method to synthesize 1,2,3-thiadiazoles. According to the Wolff method, 1,2,3-thiadiazoles are obtained by treating diazoketones with a thionating reagent. A modification of the Wolff method utilizes diazoacetonitriles and hydrogen sulfide. The method of Hurd and Mori (J Am. Chem. Soc. 77:5359, 1955) provides a reaction between hydrozones and thionyl chloride to afford 1,2,3-thiadiazole compounds, and is a preferred approach to preparing compounds of the present invention.

More specifically, compounds of the present invention may be prepared by one or more of the following general synthetic methods. One general synthetic method is illustrated in Scheme 1.

Scheme 1

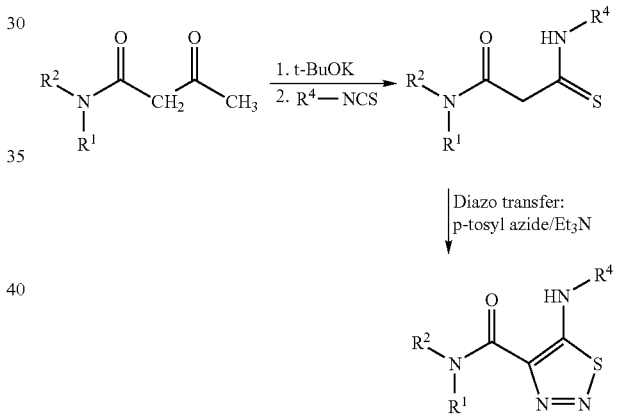

As shown in Scheme 1, a solution of t-BuOK (1 equivalent) in anhydrous THF was cooled in an ice water bath under a nitrogen atmosphere. To this solution was added an acetoacetamide compound of the formula $R^2R^1NC(=O)CH_2C(O)CH_3$ (1 equivalent) in anhydrous THF, followed by the slow (15 min.) addition of an isothiocyanate compound of the formula $R^4$—NCS (1 equivalent) with stirring. Suitable acetoacetamide and isothiocyanate compounds are commercially available and/or have been described in the chemical literature. The ice bath was removed and the reaction mixture was brought back to room temperature and stirred for about 1 hour. Water was added to the mixture and the resulting solution was kept stirring at room temperature for about 1 h. A solution of 1 N HCl solution was added to adjust the pH of the solution to about 7. The precipitate obtained was collected and dried to provide the amidoamine compound of the formula $R^2R^1NC(=O)CH_2C(S)NHR^4$.

The amidoamine compound of the formula $R^2R^1NC(=O)CH_2C(S)NHR^4$ (1 equivalent) was dissolved in a solution of anhydrous ethanol and triethylamine (1 equivalent). To this solution was added a diazo transfer agent, e.g., p-tosyl azide (1,2 equivalent). The mixture was warmed up to about 45° C. and stirred for about 30 minutes, with the formation of a significant amount of solid precipitate. The solid was collected, washed with water and dried to provide the 1,2,3-thiadiazole product shown in Scheme 1.

In Scheme 1 $R^4$ is selected from hydrogen, $R^5$, $R^6$, and $R^7$. $R^5$ is selected from alkyl, heteroalkyl, aryl and heteroaryl; $R^6$ is selected from $(R^5)_n$-alkylene, $(R^5)_n$-heteroalkylene, $(R^5)_n$-arylene and $(R^5)_n$-heteroarylene; $R^7$ is selected from $(R^6)_n$-alkylene, $(R^6)_n$-heteroalkylene, $(R^6)_n$-arylene, and $(R^6)_n$-heteroarylene; and n is selected from 0, 1, 2, 3, 4 and 5.

In one embodiment of the methodology of Scheme 1,

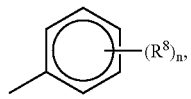

where $R^8$ is selected from hydrogen $R^5$, $R^6$, and $R^7$, where $R^5$ is selected from alkyl, heteroalkyl, aryl and heteroaryl; $R^6$ is selected from $(R^5)_n$-alkylene, $(R^5)_n$-heteroalkylene, $(R^5)_n$-arylene and $(R^5)_n$-heteroarylene; $R^7$ is selected from $(R^6)_n$-alkylene, $(R^6)_n$-heteroalkylene, $(R^6)_n$-arylene, and $(R^6)_n$-heteroarylene; and n is selected from 0, 1, 2, 3, 4 and 5.

Also in Scheme 1, each of $R^1$ and $R^2$ is independently selected from hydrogen, $R^5$, $R^6$, and $R^7$. $R^5$ is selected from alkyl, heteroalkyl, aryl and heteroaryl; $R^6$ is selected from $(R^5)_n$-alkylene, $(R^5)_n$-heteroalkylene, $(R^5)_n$-arylene and $(R^5)_n$-heteroarylene; $R^7$ is selected from $(R^6)_n$-alkylene, $(R^6)_n$-heteroalkylene, $(R^6)_n$-arylene, and $(R^6)_n$-heteroarylene ; and n is selected from 0, 1, 2, 3, 4 and 5. In formula (1), $R^1$ and $R^2$ may together form a heterocyclic structure including the nitrogen to which they are both attached.

Another general method is illustrated in Schemes 2 and 3.

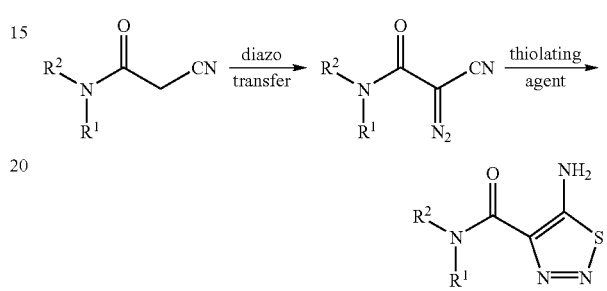

Scheme 2

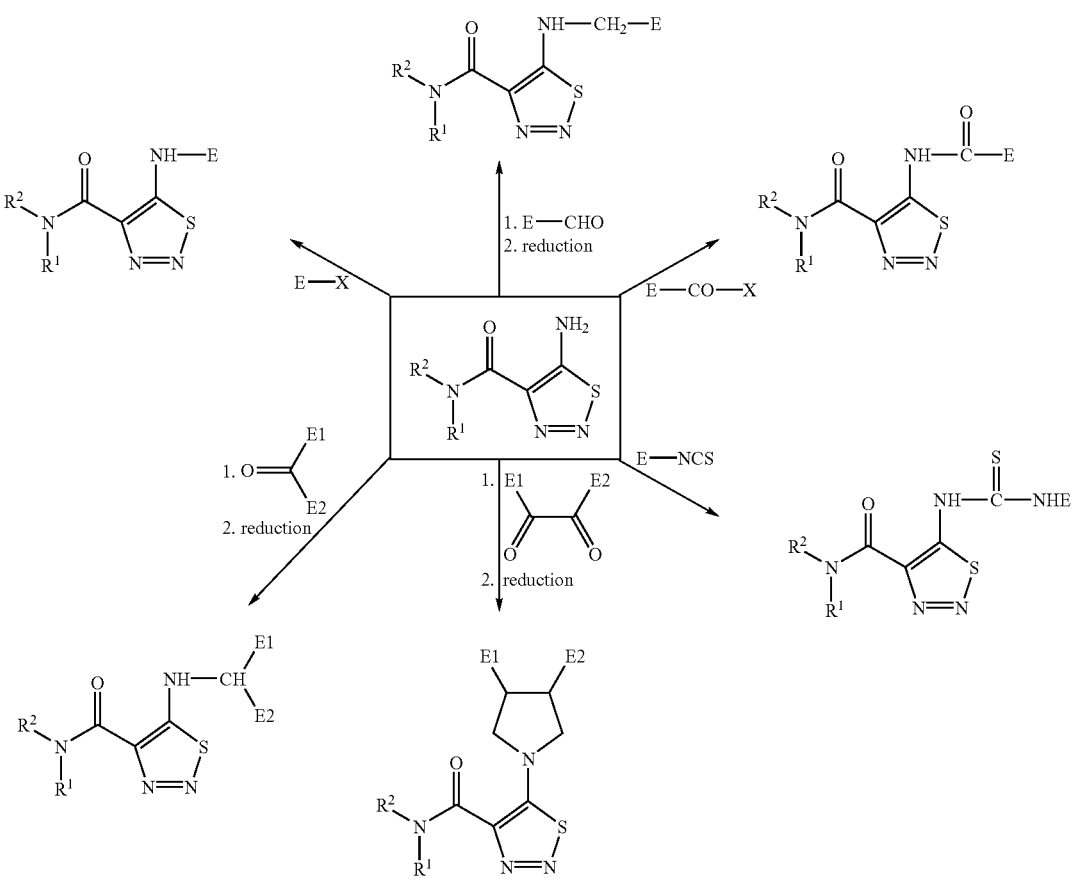

Scheme 3

As illustrated in Scheme 2, an α-cyanoamide is treated with a diazo transfer agent, e.g., p-tosyl azide, to introduce an azide group to the carbon between the carbonyl and cyano groups, i.e., the 60 -carbon. This azide compound is then treated with a thiolating agent, e.g., Lawson's agent, in order to generate a 4-amido-5-amino-1,2,3-thiadiazole compound. As illustrated in Scheme 3, the 4-amido-5-amino-1,2,3-thiadiazole compound formed by Scheme 2 is a versatile intermediate in the preparation of 1,2,3-thiadiazole compounds of the present invention.

In Scheme 3, "E", "E1" and "E2" (collectively "E") each represent a group selected from hydrogen, $R^5$, $R^6$, and $R^7$, where $R^5$ is selected from alkyl, heteroalkyl, aryl and heteroaryl; $R^6$ is selected from $(R^5)_n$-alkylene, $(R^5)_n$-heteroalkylene, $(R^5)_n$-arylene and $(R^5)_n$-heteroarylene; $R^7$ is selected from $(R^6)_n$-alkylene, $(R^6)_n$-heteroalkylene, $(R^6)_n$-arylene, and $(R^6)_n$-heteroarylene; and n is selected from 0, 1, 2, 3, 4 and 5. In one embodiment, E is selected from hydrogen, $R^5$ and $R^6$. In another embodiment, E is selected from hydrogen and $R^5$. In one embodiment, E is a hydrocarbon group.

Another general method is illustrated in Schemes 4, 5 and 6.

Scheme 4

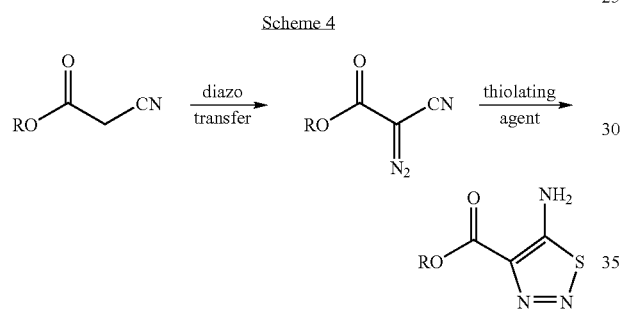

As illustrated in Scheme 4, an α-cyanocarboxylic ester is treated with a diazo transfer agent, e.g., p-tosyl azide, to introduce an azide group to the carbon between the carbonyl and cyano groups. This azide compound is then treated with a thiolating agent, e.g., Lawson's reagent, in order to generate a 4-carboxyester-5-amino-1,2,3-thiadiazole compound. As illustrated in Schemes 5 and 6, the 4-amido-5-amino-1,2,3-thiadiazole compound formed by Scheme 4 is a versatile intermediate in the preparation of 1,2,3-thiadiazole compounds of the present invention.

Scheme 5

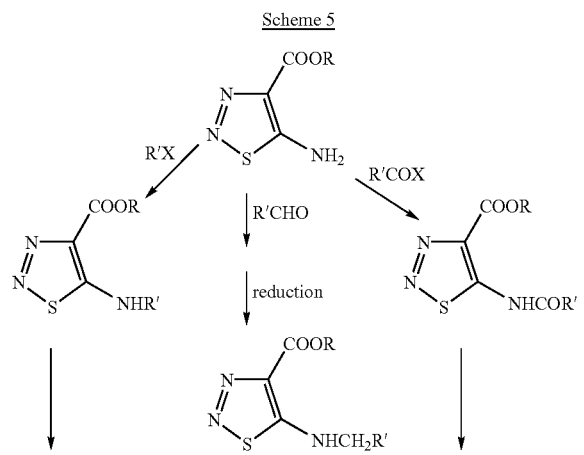

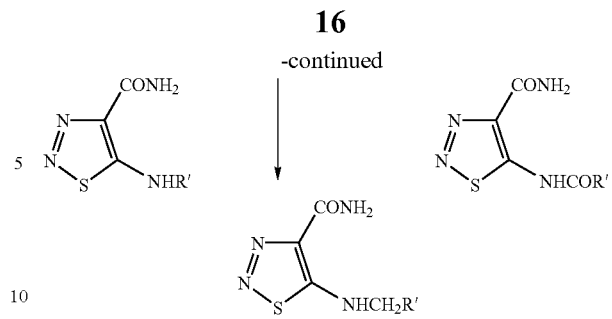

Scheme 6

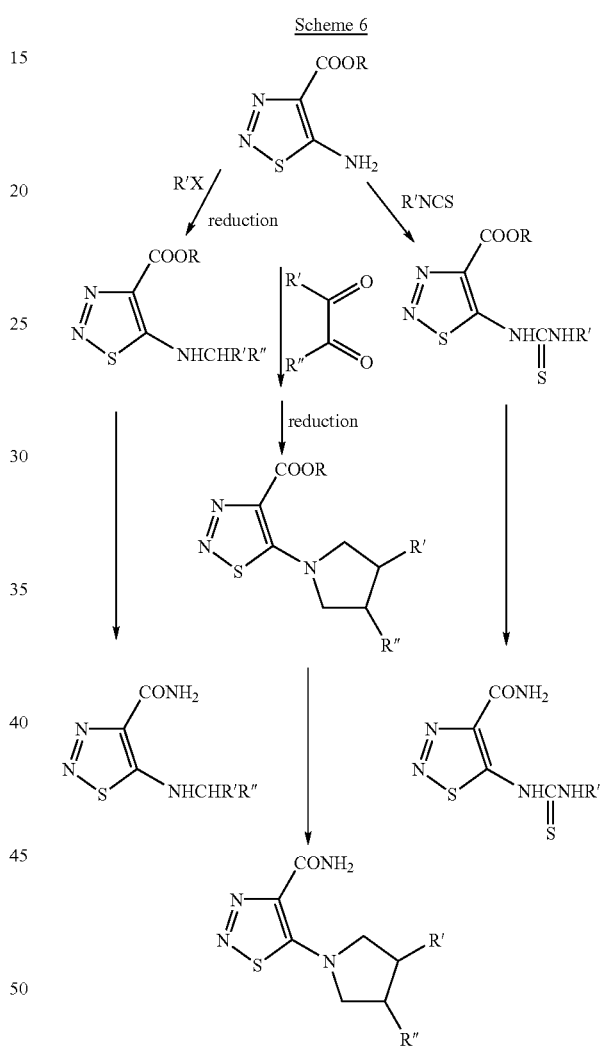

In Schemes 5 and 6, "R'", "R''" and "R'''" (collectively "R") each represent a group selected from hydrogen, $R^5$, $R^6$, and $R^7$, where $R^5$ is selected from alkyl, heteroalkyl, aryl and heteroaryl; $R^6$ is selected from $(R^5)_n$-alkylene, $(R^5)_n$-heteroalkylene, $(R^5)_n$-arylene and $(R^5)_n$-heteroarylene; $R^7$ is selected from $(R^6)_n$-alkylene, $(R^6)_n$-heteroalkylene, $(R^6)_n$-arylene, and $(R^6)_n$-heteroarylene; and n is selected from 0, 1, 2, 3, 4 and. 5. In one embodiment, R is selected from hydrogen, $R^5$ and $R^6$. In another embodiment, R is selected from hydrogen and $R^5$. In one embodiment, R is a hydrocarbon group. Another general synthetic methodology is illustrated in Scheme 7.

Scheme 7

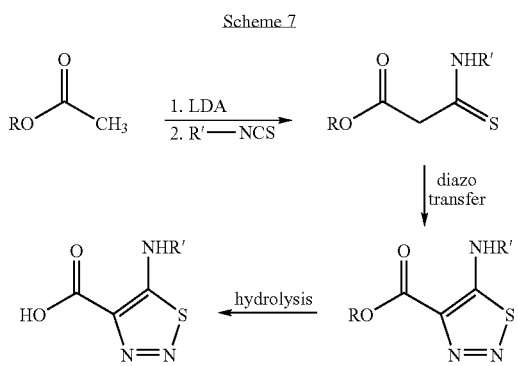

As shown in Scheme 7, an acetate ester ($CH_3$—$CO_2$—R) is treated with base, e.g., lithium diisopropylamide (LDA) at reduced temperature (typically −78° C.), followed by addition of an isothiocyanate (R'—NCS) where R' represents hydrogen, $R^5$, $R^6$, and $R^7$, where $R^5$ is selected from alkyl, heteroalkyl, aryl and heteroaryl; $R^6$ is selected from $(R^5)_n$-alkylene, $(R^5)_n$-heteroalkylene, $(R^5)_n$-arylene and $(R^5)_n$-heteroarylene; $R^7$ is selected from $(R^6)_n$-alkylene, $(R^6)_n$-heteroalkylene, $(R^6)_n$-arylene, and $(R^6)_n$-heteroarylene; and n is selected from 0, 1, 2, 3, 4 and 5. The product, R'—NH—C(=S)—$CH_2$—$CO_2$—R, is treated with a diazo transfer agent, e.g., p-tosyl azide to yield a 5-carboxylic ester-1,2,3-thiadiazole, which may be hydrolyzed to provide the corresponding 5-carboxylic acid-1,2,3-thiadiazole.

In one embodiment, R' is selected from hydrogen, $R^5$ and $R^6$. In another embodiment, R' is selected from hydrogen and $R^5$. In one embodiment, R' is a hydrocarbon group.

PHARMACEUTICAL FORMULATIONS

The compounds of this invention can be incorporated into a variety of formulations for therapeutic administration. More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intratracheal, etc., administration. The active agent may be systemic after administration or may be localized by the use of regional administration, intramural administration, or use of an implant that acts to retain the active dose at the site of implantation.

In pharmaceutical dosage forms, the compounds may be administered in the form of their pharmaceutically acceptable salts. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing the inhibitory compounds is placed in proximity to the site of the tumor, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The combined use of the provided inhibitory compounds and other cytotoxic agents has the advantages that the required dosages for the individual drugs is lower, and the effect of the different drugs complementary. Depending on the patient and condition being treated and on the administration route, the subject inhibitory compounds may be administered in dosages of 0.1 μg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus for example oral dosages in the rat may be ten times the injection dose. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For use in the subject methods, the subject compounds may be formulated with other pharmaceutically active agents, particularly other anti-metastatic, anti-tumor or anti-angiogenic agents. Angiostatic compounds of interest include angiostatin, endostatin, carboxy terminal peptides of collagen alpha (XV), etc. Cytotoxic and cytostatic agents of interest include adriamycin, alkeran, Ara-C, BICNU, busulfan, CNNU, cisplatinum, cytoxan, daunorubicin, DTIC, 5-FU, hydrea, ifosfamide, methotrexate, mithramycin, mitomycin, mitoxantrone, nitrogen mustard, velban, vincristine, vinblastine, VP-16, carboplatinum, fludarabine, gemcitabine, idarubicin, irinotecan, leustatin, navelbine, taxol, taxotere, topotecan, etc.

METHODS OF USE

The subject compounds are administered to a subject having a hyperproliferative disorders, e.g. to inhibit tumor growth, to inhibit angiogenesis, to decrease inflammation associated with a lymphoproliferative disorder, to inhibit graft rejection, or neurological damage due to tissue repair, etc. The present compounds are useful for prophylactic or therapeutic purposes. As used herein, the term "treating" is used to refer to both prevention of disease, and treatment of pre-existing conditions. The prevention of proliferation is accomplished by administration of the subject compounds prior to development of overt disease, e.g. to prevent the regrowth of tumors, prevent metastatic growth, diminish restenosis associated with cardiovascularsurgery, etc. Alternatively the compounds are used to treat ongoing disease, by stabilizing or improving the clinical symptoms of the patient.

The host, or patient, may be from any mammalian species, e.g. primate sp., particularly humans; rodents, including mice, rats and hamsters; rabbits; equines, bovines, canines, felines; etc. Animal models are of interest for experimental investigations, providing a model for treatment of human disease.

The susceptibility of a particular cell to treatment with the subject compounds may be determined by in vitro testing. Typically a culture of the cell is combined with a subject compound at varying concentrations for a period of time sufficient to allow the active agents to induce cell death or inhibit cell migration, usually between about one h and one week. For in vitro testing, cultured cells from a biopsy sample may be used. The viable cells left after treatment are then counted.

The dose will vary depending on the specific compound utilized, specific disorder, patient status, etc. Typically a therapeutic dose will be sufficient to substantially decrease the undesirable cell population in the targeted tissue, while maintaining patient viability. Treatment will generally be continued until there is a substantial reduction, e.g. at least about 50%, decrease in the cell burden, and may be continued until there are essentially none of the undesirable cells detected in the body.

The compounds also find use in the specific inhibition of signaling pathway mediated by protein kinases. Protein kinases are involved in signaling pathways for such important cellular activities as responses to extracellular signals and cell cycle checkpoints. Inhibition of specific protein kinases provides a means of intervening in these signaling pathways, for example to block the effect of an extracellular signal, to release a cell from cell cycle checkpoint, etc. Defects in the activity of protein kinases are associated with a variety of pathological or clinical conditions, where there is a defect in signaling mediated by protein kinases. Such conditions include those associated with defects in cell cycle regulation or in response to extracellular signals, e.g. hyperglycemia and diabetes Type I and Type II, immunological disorders, e.g. autoimmune and immunodeficiency diseases; hyperproliferative disorders, which may include psoriasis, arthritis, inflammation, angiogenesis, endometriosis, scarring, cancer, etc.

The compounds of the present invention are active in inhibiting purified kinase proteins, i.e. there is a decrease in the phosphorylation of a specific substrate in the presence of the compound. A protein kinase of particular interest in integrin linked kinase (ILK). ILK is a serine threonine kinase. The DNA and predicted amino acid sequence may be accessed at Genbank, no. U40282, or as published in Hannigan et al. (1996) *Nature* 379:91–96. ILK regulates integrin extracellular activity (ECM interactions) from inside the cell via its direct interaction with the integrin subunit. Interfering with ILK activity allows the specific targeting of integrin function, while leaving other essential signaling pathways intact. Increased levels of cellular ILK activity short circuits the normal requirement for adhesion to extracellular membrane in regulating cell growth. Thus, inhibiting ILK activity may inhibit anchorage-independent cell growth.

It is also known that many cell types undergo apoptosis if the appropriate contacts with extracellular matrix proteins are not maintained (anoikis). The induction of apoptosis by the subject compounds in such cells predicts an association with the ILK signaling pathway.

The compounds of the present invention bind to protein kinases at a high affinity, and find use as affinity reagents for the isolation and/or purification of such kinases. Affinity chromatography is used as a method of separating and purifying protein kinases and phosphatases using the biochemical affinity of the enzyme for inhibitors that act on it. The compounds are coupled to a matrix or gel. Preferably a microsphere or matrix is used as the support. Such supports are known in the art and commercially available. The inhibitor coupled support is used to separate an enzyme that binds to the inhibitor from a complex mixture, e.g. a cell lysate, that may optionally be partially purified. The sample mixture is contacted with the inhibitor coupled support under conditions that minimize non-specific binding. Methods known in the art include columns, gels, capillaries, etc. The unbound compounds are washed free of the resin, and the bound proteins are then eluted in a suitable buffer.

The compounds of the invention may also be useful as reagents for studying signal transduction or any of the clinical disorders listed throughout this application.

HYPER-PROLIFERATIVE DISORDERS OF INTEREST

There are many disorders associated with a dysregulation of cellular proliferation. The conditions of interest include, but are not limited to, the following conditions.

The subject methods are applied to the treatment of a variety of conditions where there is proliferation and/or migration of smooth muscle cells, and/or inflammatory cells into the intimal layer of a vessel, resulting in restricted blood flow through that vessel, i.e. neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like.

Diseases where there is hyperproliferation and tissue remodelling or repair of reproductive tissue, e.g. uterine, testicular and ovarian carcinomas, endometriosis, squamous and glandular epithelial carcinomas of the cervix, etc. are reduced in cell number by administration of the subject compounds Tumor cells are characterized by uncontrolled growth, invasion to surrounding tissues, and metastatic spread to distant sites. Growth and expansion requires an ability not only to proliferate, but also to down-modulate cell death (apoptosis) and activate angiogenesis to produce a tumor neovasculature. Angiogenesis may be inhibited by affecting the cellular ability to interact with the extracellular environment and to migrate, which is an integrin-specific function, or by regulating apoptosis of the endothelial cells. Integrins function in cell-to-cell and cell-to-extracellular matrix (ECM) adhesive interactions and transduce signals from the ECM to the cell interior and vice versa. Since these properties implicate integrin involvement in cell migration, invasion, intra- and extra-vasation, and platelet interaction, a role for integrins in tumor growth and metastasis is obvious.

Tumors of interest for treatment include carcinomas, e.g. colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies, e.g. neuroblastoma, gliomas, etc.; hematological malignancies, e.g. childhood acute leukaemia, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like.

Some cancers of particular interest include breast cancers, which are primarily adenocarcinoma subtypes. Ductal carcinoma in situ is the most common type of noninvasive breast cancer. In DCIS, the malignant cells have not metastasized through the walls of the ducts into the fatty tissue of the breast. Infiltrating (or invasive) ductal carcinoma (IDC) has metastasized through the wall of the duct and invaded the fatty tissue of the breast. Infiltrating (or invasive) lobular carcinoma (ILC) is similar to IDC, in that it has the potential metastasize elsewhere in the body. About 10% to 15% of invasive breast cancers are invasive lobular carcinomas.

Also of interest is non-small cell lung carcinoma. Non-small cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease clinically confined to the primary site, the greater the thickness and depth of local invasion of the melanoma, the higher the chance of lymph node metastases and the worse the prognosis. Melanoma can spread by local extension (through lymphatics) and/or by hematogenous routes to distant sites. Any organ may be involved by metastases, but lungs and liver are common sites.

Other hyperproliferative diseases of interest relate to epidermal hyperproliferation, tissue remodelling and repair. For example, the chronic skin inflammation of psoriasis is associated with hyperplastic epidermal keratinocytes as well as infiltrating mononuclear cells, including CD4+ memory T cells, neutrophils and macrophages.

The proliferation of immune cells is associated with a number of autoimmune and lymphoproliferative disorders. Diseases of interest include multiple sclerosis, rheumatoid arthritis and insulin dependent diabetes mellitus. Evidence suggests that abnormalities in apoptosis play a part in the pathogenesis of systemic lupus erythematosus (SLE). Other lymphoproliferative conditions the inherited disorder of lymphocyte apoptosis, which is an autoimmune lymphoproliferative syndrome, as well as a number of leukemias and lymphomas. Symptoms of allergies to environmental and food agents, as well as inflammatory bowel disease, may also be alleviated by the compounds of the invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLES

Example 1

In Vitro Screen

Compounds are screened using a series of disease related kinase targets, such as integrin linked kinase-1. Synthesized libraries of compounds are tested against each of the targets to find compounds that inhibit one of the targets preferentially. The desired in vitro potency of the inhibitor is such that the compound is useful as a therapeutic agent, i.e. in the nanomolar or micromolar range.

Inhibition of the targets is measured by scintillation counting; the incorporation of radioactive phosphate onto a specific substrate which is immobilized onto a filter paper at the end of the assay. To provide meaningful measurements of inhibition, the assays are performed both in the absence and presence of specific and known inhibitors, and the amount of incorporated radioactivity is compared to provide a baseline measurement.

The baseline activity is the amount of radioactivity incorporated in the absence of inhibitor. The amount of radioactivity incorporated in the presence of an inhibitor is called the 'sample activity', and the % inhibition is expressed by the following formula:

% inhibition=100−sample activity/baseline activity*100)

and is usually expressed in conjunction with the compound concentration. By using a range of inhibitor concentrations, the $IC_{50}$ of an inhibitor is estimated (i.e. the concentration at which enzymatic activity is reduced by 50%). The $IC_{50}$ of various compounds against a particular target can be compared, where a lower IC50 indicates a more potent compound.

Materials and Methods

Inhibition Assay: Compounds listed in Table 1 were lyophilized and stored at −20° C. Stock solutions were made by weighing out the compounds and dissolving them in dimethyl sulfoxide (DMSO) to a standard concentration, usually 20 mM, and stored at −20° C. The compounds were diluted to a starting intermediate concentration of 250 μM in 1% DMSO, then serially diluted across a row of a 96 well plate using serial 2 fold dilution steps. Diluted 100% DMSO was used as a negative control.

A volume of 5 μl of each compound dilution were robotically pipetted to Costar serocluster plates maintaining the same plate format. All assays consisted of the following volumes:

5 μl diluted compound
10 μl enzyme preparation
5 μl substrate
5 μl assay ATP and were then incubated 15 min at room temperature.

From each reaction, 10 μl of reaction mix was spotted onto Millipore Multiscreen-PH opaque plates and washed 2×10 min in 1% phosphoric acid. The plates were dried for at 40° C. for 30 min, then the substrate phosphate complexes were quantitated by scintillation counting. These Millipore plates are in a 96 well format with immobilized P81 phosphocellulose membranes. Both the phosphorylated and non-phosphorylated form of the substrate bind to the membrane while ATP (unincorporated phosphate) is removed in the subsequent wash steps. Results for various compounds of the invention are shown in Table 1 below.

Integrin Linked Kinase: The target integrin linked kinase is a full-length recombinant protein expressed in sF9 insect cells by baculovirus infection. The ILK1 substrate is CKRRRLASLR-amide.

Recombinant ILK protein was expressed using cultured insect cells and a baculovirus expression system. Standard techniques for DNA manipulation were used to produce recombinant DNA molecules and baculoviruses (Sambrook. J., Fritsch, E.F. and Maniatis, T. 1989. Molecular cloning, a laboratory manual. Second edition. Cold Spring Harbor Laboratory Press. NY; Crossen, R. and Gruenwald, S. 1998. Baculovirus expression Vector System Manual. $5^{th}$ Edition. Pharmingen, San Diego, Calif.) The ILK open reading frame (Hannigan et al., supra.), excluding the 5' and 3'untranslated regions, was inserted into the baculovirus transfer vector pAcG2T (Pharmingen) to produce a GST fusion protein under the control of the strong AcNPV polyhedrin promoter. A large scale plasmid preparation of the resulting transfer construct was made using a Qiagen Plasmid Midi Kit. This ILK transfer construct was then co-transfected with BaculoGold DNA (Pharmingen) into Sf9 insect cells (Invitrogen) and a high titre preparation of GST-ILK recombinant baculovirus was produced by amplification in Sf9 cells. Liter scale expression of GST-ILK recombinant protein was done in 1000 ml spinner flasks (Bellco) by infection of Hi5 insect cells (Invitrogen) grown in Ex-Cell 400 Serum Free Media (JRH Biosciences) at a multiplicity of infection of approximately 5. The cells were harvested three days after infection and lysed in Hypotonic Lysis Buffer (HLB; 10 mM imidazole, 5 mM EDTA, 0.1% β-mercaptoethanol, 10 ug/ml PMSF, 1 mM benzamidine) by sonication. The lysate was centrifuged at 10,000 xg for 20 min and the supernatant was discarded. The pellet was washed twice in HLB and then washed twice in High Salt Buffer (HSB; 500 mM NaCl, 10 mM imidazole, 5 mM EDTA, 0.1% β-mercaptoethanol, 10 ug/ml PMSF, 1 mM benzamidine). The pellet was then resuspended in DNAse-ATP Buffer (DAB; 10 mM $MgCl_2$, 1 mM $MnCl_2$, β-methyl aspartic acid, 2 mM NaF, 0.55 mg/ml ATP, 1 ug/ml DNAse I, 1% NP-40, 10 mM imidazole, 5 mM EDTA, 0.1% β-mercaptoethanol, 10 ug/ml PMSF, 1 mM benzamidine) and stirred for 30 min at room temperature, and then centrifuged at 10,000 xg for 20 min. The pellet was resuspended in High Salt Detergent Buffer (HDB; 1% NP-40, 1% Triton X-100, 500 mM NaCl, 10 mM imidazole, 5 mM EDTA, 0.1% β-mercaptoethanol, 10 ug/ml PMSF, 1 mM benzamidine), stirred for 30 min at room temperature, and then centrifuged at 10,000 xg for 20 min. The pellet was then washed once in each of HDB, HSB, and HLB, centrifuging at 10,000 xg each time. Finally, the pellet was resuspended in HLB.

The recombinant ILK expressed in insect cells with a baculovirus system was solubilized by treating the insoluble ILK protein with DNAse I and detergents. This produced an ILK protein preparation in the form of a microparticle suspension. This preparation had a high specific activity and was amenable to automated kinase assays.

Results:

TABLE 1

Analogues of KP-15807

| Reference Code | Chemical Names | Structure | MW | IC50 (μM) |
|---|---|---|---|---|
| KP-15807 | 5-Phenylamino-[1,2,3]thiadiazole-4-carboxylic acid amide | 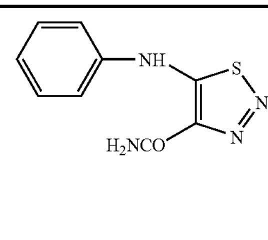 | 220.24 | 1 |

TABLE 1-continued

Analogues of KP-15807

| Reference Code | Chemical Names | Structure | MW | IC50 (μM) |
|---|---|---|---|---|
| KP-23176 | 5-Phenylamino-[1,2,3]thiadiazole-4-carboxylic acid ethyl ester | 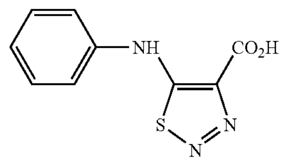 | 249.28 | 16 |
| KP-27271 | 5-Phenylamino-[1,2,3]thiadiazole-4-carboxylic acid | 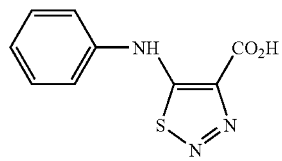 | 221.23 | >20 |
| KP 27296 | 5-(4-Bromophenylamino)-[1,2,3]thiadiazole-4-carboxylic acid amide | 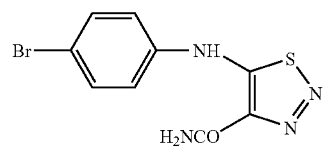 | 299.14 | >20 |
| KP 27297 | 5-(4-Methyoxyphenylamino)-[1,2,3]thiadiazole-4-carboxylic acid amide | 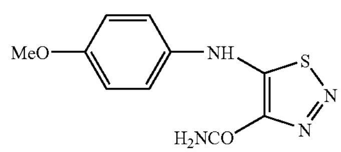 | 250.27 | >20 |
| KP 27298 | (4-Carbamoyl-[1,2,3]thiadiazol-5-yl)-carbamic acid ethyl ester | 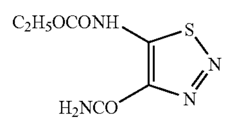 | 200.21 | >20 |
| KP 27299 | 5-(Adamantan-1-ylamino)-[1,2,3]thiadiazole-4-carboxylic acid amide | 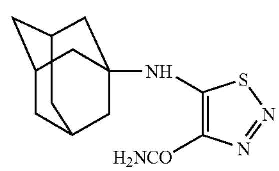 | 278.37 | >20 |
| KP 27300 | 5-Cyclohexylamino-[1,2,3]thiadiazole-4-carboxylic acid amide | 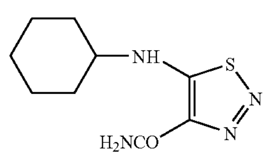 | 226.26 | >20 |
| KP 27301 | 5-(Naphthalen-1-ylamino)-[1,2,3]thiadiazole-4-carboxylic acid amide | 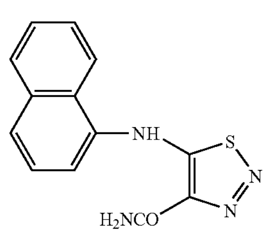 | 270.3 | 19 |
| KP 27302 | 5-Benzylamino-[1,2,3]thiadiazole-4-carboxylic acid amide | 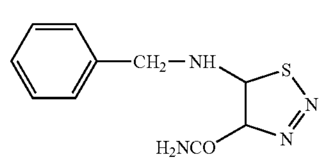 | 234.27 | >20 |

TABLE 1-continued

Analogues of KP-15807

| Reference Code | Chemical Names | Structure | MW | IC50 (μM) |
|---|---|---|---|---|
| KP 27303 | 5-Benzoylamino-[1,2,3]thiadiazole-4-carboxylic acid amide | 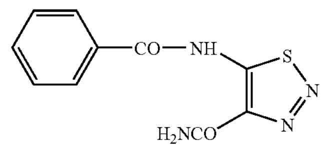 | 248.25 | >20 |
| KP 27304 | 5-Ethylamino-[1,2,3]thiadiazole-4-carboxylic acid amide | 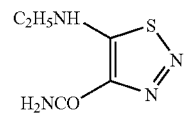 | 172.02 | >20 |
| KP 27305 | 5-Hexylamino-[1,2,3]thiadiazole-4-carboxylic acid amide | 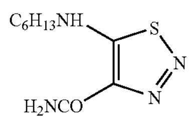 | 228.31 | >20 |
| KP 27420 | 5-(Methylphenylamino)-[1,2,3]thiadiazole-4-carboxylic acid amide | 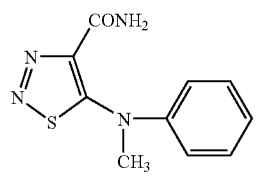 | 234.27 | >20 |
| KP 27421 | 5-Phenylamino-[1,2,3]thiadiazole-4-carboxylic acid acetylamide | 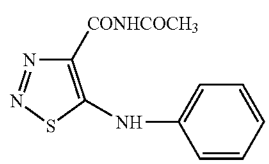 | 262.28 | >20 |
| KP 27422 | (4-Aminomethyl-[1,2,3]thiadiazol-5-yl)phenylamine | 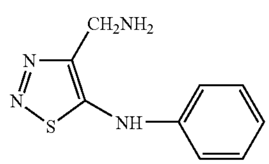 | 206.26 | >20 |
| KP 27436 | 5-(Phenyltetradecylamino)-[1,2,3]thiadiazole-4-carboxylic acid amide | 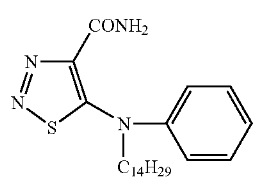 | 416.62 | ND |

Example 2

Inhibition of Angiogenesis

The test compounds were tested in several angiogenesis related assays. Angiogenesis is an important component of tumour growth and inflammation, and for this reason was deemed a descriptive model. Endothelial proliferation, thymidine incorporation proliferation, invasion and chick chorioallantoic membrane ("CAM") were models used.

Materials and Methods

Endothelial cell cultures: Cell lines used include HUVEC, EJG and MS1 and are routinely passaged 1 to 2 times weekly. Endothelial growth media (EGM) consists of Endothelial Base Media plus all supplements (Clonetics). For testing of compounds, endothelial cells were plated on 1% gelatin-coated plates. Prior to plating, gelatin solution was added to the plates for at least 10 minutes before plating, but excess solution removed immediately before adding cells. Sterile gelatin solution consists of 1% gelatin in $dH_2O$ that has been autoclaved. Endothelial cells form a characteristic cobblestone monolayer upon confluency. Typically, a T-75 plate contains 1 million microvascular cells upon confluency.

a. HUVEC Endothelial Proliferation in Response to Test compounds: HUVEC were cultured in 96-well plates and treated with a dilution series of test compounds for potential angiogenesis-related effects.

Day 0—Endothelium are plated at 5000 cells/well and at 10,000 cells/well.

Day1—Treatments are added in EGM culture medium in an appropriate dilution series (n=6 or 12). Controls included EGM alone, serum free medium (SFM), and EGM plus 0.5% DMSO.

Day 1–2, MTS/PMS solutions were added and plates read at 4 and 24 h after treatment.

TABLE 2

Results:

| Cell Treatment Conditions | MTS Relative Absorbance 4 h | MTS Relative Absorbance 24 h |
| --- | --- | --- |
| HUVEC in log phase growth | | |
| Control | 1.15 +/− 0.15 | 0.95 +/− 0.08 |
| 15807 (20 μm) | 1.25 +/− 0.03 | 1.21 +/− 0.05 |
| 15807 (10 μm) | 1.31 +/− 0.09 | 1.24 +/− 0.04 |
| 15807 (5 μm) | 1.26 +/− 0.17 | 1.22 +/− 0.09 |
| HUVEC post-confluent | | |
| Control | 2.20 +/− 0.13 | 1.47 +/− 0.27 |
| 15807 (20 μm) | 2.52 +/− 0.05 | 1.71 +/− 0.02 |
| 15807 (10 μm) | 2.30 +/− 0.05 | 1.62 +/− 0.12 |
| 15807 (5 μm) | 2.06 +/− 0.20 | 1.55 +/− 0.17 | b. Thymidine incorporation proliferation assay. Cells were plated out and grown overnight. The next day the test compound or controls were added to the plates, along with diluted $^3$H-thymidine added to a final concentration of 0.1 μCi/well, and the plates were incubated. After 24 h, the plates were spun down 1000 g for 10 min (for non-adherent cells) before removing the PBS. A volume of 120 μl of the scintillant fluid was added to each of the wells, and the plate was read.

TABLE 3

Results:
Summary of $^3$H-Thymidine Incorporation Proliferation Assay Data

| Cell Treatment Conditions | N | $^3$H-Thymidine incorporation at 24 h | $^3$H-Thymidine incorporation at 48 h |
| --- | --- | --- | --- |
| HUVEC in log phase growth | | | |
| Control | 6 | 854 +/− 113 | 1274 +/− 216 |
| KP 15807 (10 μm) | 6 | 746 +/− 200 | 1251 +/− 117 |
| HUVEC post-confluent | | | |
| Control | 6 | 694 +/− 19 | 676 +/− 63 |
| KP 15807 (10 μm) | 6 | 571 +/− 86 | 452 +/− 71* | c. Invasion Assays: Invasion of cells into surrounding tissue is a hallmark property of tissue remodeling. Tissue remodeling occurs during most pathological progression, including tumor progression, angiogenesis and during normal processes such as wound healing. The following invasion assays were performed using Biocoat® Cell Environments™ Matrigel Invasion Chamber 24-Well Plate Size (Becton Dickinson). The invasion chambers can be used to assess the ability of a cell to traverse an extracellular matrix under a variety of conditions. The chambers consist of a 24 well plate and 12 inserts that can be suspended in each well and act as an upper chamber. Cells place in the upper chamber insert must invade through a matrix in order to enter the lower chamber.

Cells were pre-labeled with $^3$H-thymidine overnight. Typically, 5×10$^5$ cells were cultured overnight in 5 mls of serum-containing media spiked with 200 μl of thymidine stock solution. Cells were scraped off of the flask substratum and gently pipetted up and down to achieve single cell suspension in the medium. Cell numbers were estimated using a hemocytometer.

Approximately 2×10$^5$ cells were added to a 6 well plate in 1 ml serum-containing media and then allowed to attach and invade through a matrix towards a chemoattractant in the lower chamber overnight. The bottom chamber or well of the 24 well plate contained with 1 ml of serum containing media and either 10 ng/ml of vitronectin or fibronectin as chemoattractant.

After an incubation period of 24 h, media was carefully removed from the upper chamber insert and saved for scintillation counting. Cells that did not invade were removed from the upper surface of the filter using a cotton swab. The filters containing cells that had invaded the matrix were removed carefully from the chamber insert with a scalpel and placed in scintillation vials. The media was also collected from the lower chamber and placed in a scintillation vial. The relative amount of cell invasion was calculated by adding counts from the filters and lower chambers and dividing this sum by the total counts added initially to the upper chambers. The percentage of total counts that invaded was compared between drug-treated and untreated groups.

TABLE 4

Results:
Summary of Invasion Assay Data

| Cell Treatment Conditions | N | % Cell Invasion |
| --- | --- | --- |
| IEC-18 Epithelium | | |
| Control | 6 | 16.8 |
| 15807 (10 μm) | 6 | 9 |
| IEC-18-13 Epithelium | | |
| Control | 6 | 34.9 |
| 15807 (10 μm) | 6 | 8 |

Chick chorioallantoic membrane assay (CAM assay): was performed on fertilized chicken eggs and used as a test for angiogenesis inhibition.

Approximately 4 dozen fertilized eggs were sprayed with 70% ETOH and placed in a 180 egg incubator (GQF Sportsman incubator). The eggs were incubated "rounded-side down" and were fully rotated along the vertical axis every 30 minutes at 37° C. under 90% relative humidity.

After 4 days, the eggs were placed upside down (round side up) for 5–10 minutes, before a round hole approximately 3 centimeters in diameter was created above the pointed end or "air hole" of the egg using sterile blunt-ended forceps ("deshelling"). The inner membrane was also removed, and the embryo was visible through this opening. A small portion of the outer membrane was then carefully removed using fine-tipped forceps in order to expose the CAM. Sterile Parafilm was placed over the de-shelled opening to create an airtight seal. The eggs were returned to the incubator (with no rotation) for 2 days.

Viable eggs were then treated with control and inhibitor compounds. Gelfoam[198] gelatin sterile sponge (Upjohn) or 1–2 mm discs of methylcellulose saturated with physiological saline, buffer or an appropriate dilution of the compounds under investigation. The Gelfoam[198] fragments of methylcellulose discs were added directly to the surface of the developing CAM. Care was taken not to add the treatment directly over a large vessel. The shells were marked in 3 places to aid in stereotactic localization of the treatment sponge or disc. An average of 6 eggs were included for each experimental condition. The treated eggs were returned to the incubator for 2 days.

The eggs were then assessed for blood vessel growth inhibition. Photomicrographs for records and visual examination were made using a Nikon dissecting microscope with an attached Nikon 35-mm camera body.

TABLE 5

Results:
Data from CAM Developmental Angiogenesis Assay

| Treatment | N | % Inhibition |
|---|---|---|
| Adjuvant Control (DMSO) | 13 | 0 |
| 15807 (20 µm) | 25 | 85 |
| 15807 (10 µm) | 8 | 75 |
| 15807 (5 µm) | 8 | 60 |
| HBS | 4 | 0 |
| KP-27301 (50 µM) | 6 | 100% |
| KP-27304 (50 µM) | 5 | 60% |

Example 3

Assessment of Inhibitor Effects on Cell Viability

Two assays (MTT and $^3$H-thymidine incorporation) were performed at one concentration to screen for cellular toxicity, and were followed up with a third assay (Caspase-3) on compounds that had cytotoxic effects, to determine the mechanism of death, either necrosis or apoptosis. Apoptosis is an important indicator of a potential therapeutic agent for treating hyperproliferative disease, such as cancer and precancerous conditions. In addition, inflammation, as well as angiogenesis, can be linked to a suppression of apoptosis. Inflammation results from proliferation of immune cells (T-cells, macrophages, neutrophils, etc), particularly immune cells producing pro-inflammatory cytokines, and results in increased vascularization of the affected area. Inducing apoptosis in immune cells and inhibiting angiogenesis combats the processes contributing to of inflammatory disease.

Each experiment was done 3 times, with 8 well replicates each time.

MTS is a colorimetric assay that gives a measure of mitochondrial enzyme activity and helps determine how actively a cell population is metabolizing. $^3$H thymidine incorporation is an assay that indicates how actively the cells are incorporating DNA after treatment with the compound. Results from these two assays determine the classification of a compound as neutral, cytostatic, cytotoxic, or apoptotic.

|  | High MTS | Low MTS |
|---|---|---|
| High $^3$H-thymidine incorporation | Neutral | Contact inhibited cell line or slowly apoptosis inducing |
| Low $^3$H-thymidine incorporation | Cytostatic | Cytotoxic |

Assays for apoptosis were performed on compounds that showed cytotoxic results on some of the cell lines. The assay is based on an enzyme (Caspase 3) that is induced in early apoptosis.

Potency of a compound on cell lines is determined by comparing results of treated cells to untreated controls. Cells are also treated with a standard control (vincristine sulfate) to ensure that the cells are responsive and were not damaged during seeding of the cells.

Screening of compounds on Cell lines using MTS as a measure of viability and $^3$H-thymidine incorporation as a measure of proliferation or DNA uptake. Cells were grown and maintained in log phase of growth in T75 flasks. When ready to perform the experiment, a known number of cells were seeded in 100 µl aliquots into 96 well plates using the cell lines: A549/ATCC, Non-Small Cell Lung Cancer; H460 Lung Cancer, Lewis Lung Carcinoma (Murine): Lung Cancer; Colon Cancer; COLO 205, Colon Cancer, SW-480, Colon Cancer; HCT-116, Colon Cancer; HT29; CNS Cancer; U251, CNS Cancer; U87, Melanoma; MALME-3M, Melanoma; Melanoma; SK-MEL-28, Melanoma; SK-MEL-5, Melanoma; B16, F1 (Murine), Melanoma; B16 F10 Murine Melanoma; Ovarian Cancer; OVCAR-3, Ovarian Cancer; OVCAR-5, Ovarian Cancer, SK-OV-3, PC-3, Prostate Cancer; DU-145, Prostate Cancer; LNCaP, Prostate Cancer; MCF7, Breast Cancer; MDA-MB-231/ATCC, Breast Cancer; Breast Cancer; SK-BR-3. Enough plates were seeded to allow one plate for MTS studies and one plate for $^3$H-thymidine incorporation. Cells were then allowed to grow for 48–72 h in medium, at which time the test compound was added at twice the desired concentration (diluted in 100 µl medium, the final DMSO concentration was 0.01%). Cells were exposed to the test compound for 72 h, and cell viability and $^3$H-thymidine uptake were assessed.

Viability using MTS. Stock MTS/PMS solution was added to each well at 1/10 the original culture volume (i.e. 20 µl per well) and the plate incubated for 4 and 24 h periods. At the end of the incubation periods, medium can remain and converted dye solution read directly in the well. Dissolved converted dye is measured at 490 nm in the ELISA plate reader at 4 or 24 h $^3$H-thymidine incorporation. Stock $^3$H thymidine is diluted to 1 µCi per ml, 100 µl of the solution is added to each well) and the plate incubated for a 4 h period. At the end of the 4 h, the medium is removed by aspiration. The plate is rinsed once in PBS and PBS removed by aspiration. For non-adherent cells, the plate is spun down at 1000 g for 10 min before removing the PBS. The plates are allowed to dry, and 120 µl of scintillation cocktail is added to each well. Plates are counted in the Wallac Beta Trilux counter.

Assessment of apoptosis: is performed with ApoAlert[198] CPP32/Caspase-3 Assay Kits (Clontech, Palo Alto Calif.), in accordance with the manufacturer's instructions (see Casciola-Rosen et al. (1996) *J. Exp. Med.* 183:1957–1964; and Fernandes-Alnemri et al. (1994) *J. Biol. Chem.* 269:30761–30764). Briefly, the assay relies on the activation of the ICE family proteases during initiation of apoptosis. The detection of cell death due to apoptosis relies on the cleavage of specific protease substrates, which are assayed by colorimetric or fluorometric methods. CPP32 protease is specifically inhibited by the synthetic tetrapeptides, DEVD—CHO and DEVD—fmk. DEVD—CHO is a reversible inhibitor; DEVD—fmk is irreversible. When assaying whole cell lysates, these inhibitors are used in negative control assays to assess the fluorescence contribution of the normal subpopulation of apoptotic cells.

MitoSensor Apoptosis Assay

The cationic dye called MitoSensor (Clontech K2017-1) fluoresces differently in apoptotic and nonapoptotic cells. In healthy cells, the MitoSensor stain is taken up in the mitochondria, where it forms aggregates exhibiting intense red/orange fluorescence. In apoptotic cells, the altered mitochondrial membrane potential does not allow the MitoSensor stain to aggregate. As a result, the dye remains in monomeric form in the cytoplasm, where it fluoresces green. The different fluorescent characteristics of healthy versus apoptotic cells can be detected by flow cytometry or fluorescence microscopy.

Materials and Methods

The Clontech MitoSensor dye (Clontech K2017-1) was used as follows according to the manufacturer's instructions (protocol PT3308-2). The cell line IEC18-13 (a stable transfectant cell line overexpressing ILK) was seeded to a 24 well tissue culture plate (Costar 3526) at $2\times10^4$ cells per well in 400 μl of αMEM media (Gibco BRL 12000-014) with 10 μg/ml insulin and 5% fetal bovine serum (Gibco BRL). These were cultured overnight at 37° C. and 5% $CO_2$. The cells were then treated with therapeutic compound at 5 μM final concentration in the media. An untreated negative control was included in the treatment set. The cells were incubated another 24 h. at 37° C. and 5% $CO_2$. MitoSensor staining was carried out by first rinsing the cells once with serum free αMEM and removing the rinse. Then, 1 μl of MitoSensor reagent was added to 1 ml of Incubation Buffer to a final concentration of 5 μg/ml and this was vortexed briefly. Then, 1 ml of the diluted MitoSensor was added per well of the 24 well plate and the cells were incubated at 37° C. and 5% $CO_2$ for 15–20 min. The cells were gently rinsed once with serum free αMEM and then 400 μl of serum free αMEM was added before observation by fluorescence microscopy.

Results

The untreated controls grown in αMEM with 10 μg/ml insulin and 5% fetal bovine serum for 24 h gave approximately 75% orange (healthy) and 25% green (apoptotic) staining cells, indicating that the majority of cells were non-apoptotic.

In contrast, the cells treated with the subject compounds under the same conditions gave approximately 22% orange (healthy) and 78% green (apoptotic) cells, indicating that treatment with compounds in the 15807 family had a significant effect on inducing apoptosis in cells. The ability to induce apoptosis is significant for the therapeutic effectiveness of the compounds.

Example 4

Synthesis of 5-Phenylamino-[1,2,3]thiadiazole-4-carboxylic acid amide

To an ice cooled THF solution of t-BuOK (1.0 mmol) in a flask was added acetoacetamide (0.10 g, 1.0 mmol) in anhydrous THF. Phenyl isothiocyanate solution (0.15 g, 1.1 mmol) was added slowly to the flask with stirring 15 minutes after the addition of acetoacetamide. The reaction mixture was stirred at room temperature for about 2 h. Then 2 mL of water was added to the reaction mixture and it was kept stirring at room temperature for about 1 h. The pH of the solution was adjusted with 2 N HCl solution to about 5. The organic layer was separated and the solvent was removed. The solid obtained was then dissolved in anhydrous ethanol. Triethylamine (0.1 mL) and p-tosyl azide (0.2 g, 1.0 mmol) were added to the solution sequentially. The mixture was warmed up to 45° C. and stirred for about 30 minutes. The solid precipitate from the reaction mixture was collected, washed with cold ethanol and dried. This process yielded 0.14 g (64%) of the desired product, characterized as follows: m.p.: 195–197° C. $^1$H NMR (ppm, in DMSO—$d_6$): 11.01 (s, 1 H), 8.36 (s, 1 H), 7.88 (s, 1 H), 7.15–7.60 (m, 5 H). FTIR ($cm^{-1}$, KBr pellet): 3367, 1680, 1648, 1595, 1551, 1470, 1449, 1313, 1251, 1080, 877, 793, 747, 650. Mass spectrum (EI): 220 (75%, $M^+$), 192, (42%, $(M-28)^+$), 77 (100%, $C_6H_5^+$).

Example 5

Additional compounds prepared by method of Example 4

The following 1,2,3-thiadiazole compounds were prepared essentially according to the method outlined above, using the corresponding acetoacetamide and isothiocyanate compounds:

5-(4-Bromophenylamino)-[1,2,3]thiadiazole-4-carboxylic acid amide;

5-(4-Methoxyphenylamino)-[1,2,3]thiadiazole-4-carboxylic acid amide;

(4-Carbamoyl-[1,2,3]thiadiazol-5-yl)-carbamic acid ethyl ester;

5-(Adamantan-1-ylamino)-[1,2,3]thiadiazole-4-carboxylic acid amide; 5-Cyclohexylamino-[1,2,3]thiadiazole-4-carboxylic acid amide;

5-(Naphthalen-1-ylamino)-[1,2,3]thiadiazole-4-carboxylic acid amide;

5-Benzylamino-[1,2,3]thiadiazole-4-carboxylic acid amide; 5-Benzoylamino-[1,2,3]thiadiazole-4-carboxylic acid amide; 5-Ethylamino-[1,2,3]thiadiazole-4-carboxylic acid amide; 5-Hexylamino-[1,2,3]thiadiazole-4-carboxylic acid amide;

Example 6

Synthesis of 5-Phenylamino-[1,2,3]thiadiazole-4-carboxylic acid ethyl ester

Following the general procedure outlined in Scheme 7, a solution of n-BuLi (28 mmol) in anhydrous THF (50 mL) at −78° C. under an argon atmosphere was slowly treated with diisopropylamine (3.45 g, 34 mmol). This mixture was kept stirring at −78 °C. for 30 minutes. Ethyl acetate (2.53 g, 29 mmol) was slowly added into the mixture and the reaction was kept going for another 20 minutes after the addition of ethyl acetate. Phenyl isothiocyanate (3.89 g, 29 mmol) was slowly added into the reaction mixture. The reaction mixture was kept stirring at −78° C. for one h. A solution of saturated aqueous ammonium chloride (100 mL) was added to the reaction mixture and the pH of the solution was about 8–9. The resulting solution was extracted with ethyl acetate (2×50 mL). The organic layers were combined and then dried with anhydrous $Na_2SO_4$. Light yellow brown oil was obtained after removal of the solvent. This oil was used without purification in the next step of the reaction.

To a solution of the ester obtained above in anhydrous ethanol (1.02 g, 4.6 mmol) was added triethylamine (0.56 g, 5.6 mmol) and p-tosyl azide (0.92 g, 4.7 mmol). The reaction mixture was warmed up to 45° C. and stirred at room temperature for about 1 h. The residue obtained after the removal of the solvent was purified by column chromatography with $CHCl_3$ as the eluant. The product was obtained as a white powder (0.21 g, 18%). m.p.: 87–89° C. $^1$H NMR (ppm, $CDCl_3$): 10.18 (s, br, 1 H), 7.3–7.5 (m, 2 H), 7.1–7.2 (m, 3 H), 4.50 (q, 2 H, J=8 Hz), 1.52 (t, 3 H, J=8 Hz). FTIR ($cm^{-1}$, KBr pellet): 3240, 3204, 2974, 1671, 1594, 1548, 1453, 1430, 1309, 1222, 1200, 1026, 759, 687.

Example 7

Synthesis of 5-Phenylamino-[1,2,3]thiadiazole-4-carboxylic acid

A suspension of 5-phenylamino-[1,2,3]thiadiazole-4-carboxylic acid ethyl ester(0.1 g, 0.4 mmol, prepared as above) in 10 ml of 10% NaOH solution was stirred at room temperature for 1.5 h. The pH of the solution was adjusted with 5% HCl solution to about 2. The solution was extracted with $CHCl_3$ (2×20 mL). The organic layer was dried with anhydrous $Na_2SO_4$. The product was obtained as an off-white solid after the removal of the solvent (0.06 g, 67%). m.p.: 165° C. (decomp.). $^1H$ NMR (ppm, DMSO—$d_6$): 10.22 (s, br., 1H), 7.3–7.7 (m, 5 H). FTIR ($cm^{-1}$, KBr pellet): 3407, 3024, 1673, 1524, 1501, 1464, 1340, 1266, 1090, 784, 754.

Example 8

Synthesis of 5-Phenylamino-[1,2,3]thiadiazole-4-carboxylic acid acetylamide

To an ice-cooled suspension of NaH (16 mg 60% in oil, 0.23 mmol) in 1.5 mL of DMF was added 0.5 mL of DMF solution of 5-phenylamino-[1,2,3]thiadiazole-4-carboxylic acid amide (50 mg, 0.23 mmole). The mixture was stirred at room temperature for 1 h, and then cooled in an ice bath. To the cooled solution was added acetyl chloride (18.6 mg, 0.24 mmole), resulting in the. formation of a yellowish solution that was kept stirring at room temperature for 1.5 h. The reaction was then quenched with a mixture of 5 mL of saturated aqueous $NH_4Cl$, 5 mL of saturated aqueous NaCl and 5 mL of EtOAc. The aqueous phase was extracted with EtOAc (2×6 mL). The combined organic layers were dried with $Na_2SO_4$, concentrated, and then loaded onto a preparative TLC plate, which was sequentially eluted with hexane-EtOAc (2:1) and EtOAc-acetone-$H_2O$ (4:1:0.15). The product (24 mg) was obtained as a yellowish solid. $^1H$ NMR (ppm, in DMSO-$d_6$): 12.84 (s, br., 1 H), 7.79 (d, 2 H), 7.64 (s, br., 1 H), 7.53 (t, 2 H), 7.40 (t, 1 H), 2.39 (s, 3 H).

Example 9

Synthesis of 5-(Methylphenylamino)-[1,2,3]thiadiazole-4-carboxylic acid amide

Following the procedure of Example 5, and using 5-phenylamino-[1,2,3]thiadiazole-4-carboxylic acid amide (50 mg, 0.23 mmol) and iodomethane (33.7 mg, 0.24 mmol) yielded 10 mg of the named product as a white powder. m.p. 194–196° C. $^1H$ NMR (ppm, in DMSO-$d_6$): 8.01 (s, br., 1 H), 7.70–7.55 (m, 6 H), 2.42 (s, 3 H). FTIR ($cm^{-1}$, KBr pellet): 3395, 3293, 3176, 2928, 1685, 1654, 1618, 1499, 1386, 1299, 999, 766, 743, 691. MS (El) 234 ($M^+$, 12%), 206 (M—$N_2$, 38%), 77 ($C_6H_5^+$, 100%), 51 (44%).

Example 10

Synthesis of (4-Aminomethyl-[1,2,3]thiadiazol-5-yl)phenylamine

To a suspension of $NaBH_4$ (129 mg, 3.4 mmole) and 5-phenylamino-[1,2,3]thiadiazole-4-carboxylic acid amide (150 mg, 0.68 mmole) in 2.5 mL of dioxane was added 0.5 mL of a dioxane solution of acetic acid (204 mg, 3.4 mmol) dropwise. The resulting yellow-greenish mixture was refluxed for about 3 h, and then cooled to room temperature to yield a colorless mixture. The colorless mixture was treated with a mixture of 5 mL $CH_2Cl_2$—MeOH (5:1) and 5 mL saturated aqueous $NH_4Cl$. The aqueous layer was extracted with $CH_2Cl_2$—MeOH (5:1, 3×7 mL). The combined organic layers were dried over anhydrous $Na_2SO_4$, filtered, concentrated and then purified by column chromatography (silica gel (240–400 μm), $CH_2Cl_2$—MeOH, 10:1). The product (15 mg) was obtained as a pale brownish powder. $^1H$ NMR (ppm, in DMSO-$d_6$): 7.54–7.30 (m, 3 H), 7.20 (d, 2 H), 7.07 (t, 1 H), 4.22 (s, 2 H), 3.80 (s, br., exchanged with $D_2O$). FTIR ($cm^{-1}$, KBr pellet): 3369, 3048, 2930, 1601, 1546, 1499, 1465, 1226, 749, 692.

Example 11

Synthesis of 5-(Phenyltetradecylamino)-[1,2,3]thiadiazole-4-carboxylic acid amide To an ice-cooled suspension of NaH (19 mg, 60 wt % in oil, 0.46 mmole) in 3 mL of DMF was added 5-phenylamino-[1,2,3]thiadiazole-4-carboxylic acid amide (100 mg, 0.46 mmole). The mixture was stirred at room temperature for 1 h. 1-Bromotetradecane (131 mg, 0.47 mmole) was then added to the reaction mixture which was cooled in an ice bath. The reaction was carried out overnight with stirring and then quenched with a mixture of 5 mL of saturated aqueous $NH_4Cl$, 5 mL of saturated aqueous NaCl and 10 mL EtOAc. The aqueous layer was extracted with EtOAc (2×10 mL). The combined organic layers were dried with anhydrous $Na_2SO_4$, concentrated and then purified by preparative TLC with hexane:EtOAc (1:1) as the eluant. A white powder product was obtained (122 mg, 66%). m.p. 79–81° C. $^1H$ NMR (ppm, $CDCl_3$): 7.60–7.44 (m, 5 H), 7.20 (s, br., 1 H), 5.63 (s, br., 1 H), 2.96 (t, 2 H), 1.43–1.00 (m, 24 H), 0.88 (t, 3 H). FTIR ($cm^{-1}$, KBr pellet): 3386, 3299, 2918, 2851, 1674, 1657, 1600, 1527, 1503, 1384, 1299, 999, 766, 743, 693.

Example 12

Synthesis of N-(5-Phenylamino-[1,2,3]thiadiazol-4-ylmethyl)guanidine

To a 2 mL pyridine solution of 5-phenylamino-[1,2,3]thiadiazole-4-carboxylic acid amide (50 mg, 0.24 mmole), was added the powder of 1H-pyrazole-1-carboxamidine hydrochloride (235 mg, 1.59 mmole) and diisopropyl ethylamine (234 mg, 1.8 mmole). Then the mixture was heated to about 80 ° C. The reaction mixture was cooled to room temperature for 4 hours and the solvent was then evaporated. The residue was loaded onto a preparative TLC plate and eluted sequentially with neat $CH_2Cl_2$ and $CH_2Cl_2$.MeOH (4:1). A 94 mg of crude product was collected, which was further purified by another preparative TLC (silica gel, $CH_2Cl_2$.MeOH.$H_2O$=3.6:0.4:0.06). The title compound was obtained in 40 mg (66%). $^1H$ NMR (ppm, $CDCl_3$): 9.33 (br. t, 1 H), 8.01 (br. s, 1 H), 7.63–7.82 (m, 2 H), 7.20–7.40 (m, 3 H), 6.37 (br. s, 2 H), 6.08 (br. s, 1 H), 4.41 (d, 2 H).

Example 13

Synthesis of 5-Phenylamino-[1,2,3]thiadiazole-4-carbothioic acid amide

Lawesson's reagent (202 mg, 0.5 mmole), 5-phenylamino-[1,2,3]thiadiazole-4-carboxylic acid amide (220 mg, 1 mmole), and 1.5 mL HMPA was mixed in a 10 mL flask. This mixture was heated to 80° C. and a pale-yellowish solution was obtained. After the reaction was carried out overnight, another 200 mg of Lawesson's reagent was added. The reaction was stopped one hour later by the addition of aqueous saturated NaCl to the reaction mixture. This solution was then extracted with $CH_2Cl_2$ (3×6 mL), and the combined organic phase was washed with saline (3×5 mL), and then dried with anhydrous $MgSO_4$. One third of the reaction mixture was purified by preparative TLC yielding 22 mg pale yellow powder. IR ($cm^{-1}$, KBr pellet): 3454, 3306, 3159, 2932, 1596, 1556, 1498, 1462, 1451, 1427, 1322, 876, 864, 784, 748, 554. $^1$H NMR (ppm, in DMSO-$d_6$): two isomers were observed in the NMR spectrum: the major isomer: 12.63 (br. s, 1 H), 9.95 and 9.85 (br. s, NH$_2$), 7.20–7.59 (m, 5 H); the minor isomer: 11.80 (br. s, 1 H), 9.06 (br. s, NH$_2$), 7.40–7.67 (m, 5 H).

Example 14

Synthesis of 5-Phenylamino-[1,2,3]thiadiazole-4-carboxylic acid (2-morpholin-4-yl-ethyl)amide To a solution of N-aminoethylmorpholine (228 mg, 10 mmole) in 2 mL anhydrous THF at −40° C. was added 0.8 mL of 2 M n-BuLi solution in cyclohexane. Some white solid was precipitated instantly. The suspension was stirred for about a half an hour. When the bath temperature reached −10° C., a solution of 5-phenylamino-[1,2,3]thiadiazole-4-carboxylic acid ethyl ester (60 mg, 0.24 mmole) in anhydrous THF was added to the mixture. After it was stirred at room temperature for an hour, the reaction was quenched with saturated NH$_4$Cl solution. The solution was extracted with EtOAc and residue obtained after the removal of EtOAc was purified by preparative TLC (silica gel, CH$_2$Cl$_2$.MeOH=15:1). The title compound was isolated as a white powder in 60% yield (48 mg). $^1$H NMR (ppm, in CDCl$_3$): 10.91 (br. s, 1 H), 7.77 (br. s, 1 H), 7.00–7.60 (m, 5 H), 3.70 (m, 4 H), 2.60 (m, 4 H).

Example 15

Synthesis of 5-phenylamino-1,2,3]-thiadiazole-4-carboxylic acid morpholin-4-ylamide This compound was synthesized the same way as described in Example 14. N-Aminomorpholine (180 mg, 10 mmole) and 5-phenylamino-[1,2,3]thiadiazole-4-carboxylic acid ethyl este (60 mg, 0.24 mmole) yielded 65 mg of white powder with 88% yield. $^1$H NMR (ppm, in CDCl$_3$): 10.92 (br. s, 1 H), 8.04 (br. s, 1 H), 6.95–7.56 (m, 5 H), 3.90 (m, 4 H), 3.00 (m, 4 H).

Example 16

Synthesis of 5-Phenylamino-[1,2,3]thiadiazole-4-carboxylic acid hydrazide

5-Phenylamino-[1,2,3]thiadiazole-4-carboxylic acid ethyl ester (60 mg, 0.24 mmole), 40% hydrazine in water (1 mL) and 0.2 mL MeOH were mixed in a 10 mL flask. The solution was stirred at room temperature overnight. After evaporation of the solvent, the residue was mixed with MeOH to give a white powder suspension. The crude product was collected by filtration. A pure compound was obtained by preparative TLC of part of the product which gave 5 mg of the purified compound. $^1$H NMR (ppm, in DMSO-$d_6$): 10.90 (br. s, 1 H), 7.83 (m, 2 H), 7.45 (m, 2 H), 7.40 (m, 1 H), 4.60 (br. s, 1 H). Note: some NHs may be exchanged with H$_2$O at 3.37 ppm (br. s).

Example 17

Synthesis of 5-Phenylamino-[1,2,3[thiadiazole-4-carboxylic acid methylamide

To a solution of 2 M NH$_2$CH$_3$ in cyclohexane (2 mL) at −40° C. was added 0.8 mL of 2 M n-BuLi in cyclohexane under argon. A white precipitate was immediately observed. The mixture was stirred at −30° C. for 0.5 hours, and 5-phenylamino-[1,2,3]thiadiazole4-carboxylic acid ethyl ester (60 mg, 0.24 mmole) in 1 mL of cyclohexane was slowly added. Greenish solution was immediately obtained. The reaction was slowly warmed up to room temperature and TLC showed a total disappearance of the starting material. A mixture of 7 mL of saturated NH$_4$Cl solution and 7 mL of EtOAc was added to the ice-cooled flask and the solution was stirred for 30 minutes. The aqueous layer was neutralized to pH ~7 and then extracted with EtOAc. The organic layer was absorbed with silica gel, loaded to a 53 g silica gel column, and eluted with hexane:EtOAc=5:1. A 25 mg white powder was obtained (45 %). $^1$H NMR (ppm, DMSO-$d_6$): 11.00 (br. s, 1 H), 8.92 (br. q, 1 H), 7.46 (t, 2 H), 7.34 (d, 2 H), 7.20 (t, 1 H), 2.85 (d, 3 H).

Example 18

Synthesis of 5-(Benzothiazol-2-ylamino)-[1,2,3]thiadiazole-4-carboxylic acid ethyl ester Sodium hydride (60 mg of a 60% by wt slurry in mineral oil, 1.5 mmol) was placed in a dry 25 mL round bottom flask under nitrogen. Anhydrous THF (1.5 mL) was added to the flask. The sodium hydride was washed by allowing the solids to settle and then extracting the liquid off using a syringe. Fresh THF (1.0 mL) was added to the flask and the slurry was cooled in an ice bath. A solution of 5-phenylamino-[1,2,3]thiadiazole-4-carboxylic acid ethyl ester was prepared in 1.0 mL of THF and added dropwise to the solution of the sodium hydride over five minutes. The flask containing the thiadiazole was rinsed with an additional 1.0 mL of THF which was then introduced into the reaction flask. The reaction solution was allowed to warm to room temperature and 2-chlorobenzothiazole (93 μL, 0.71 mmol) was added neat via a micropipette. Tetrabutylammonium bromide (288 mg, 0.89 mmol) was then introduced and the reaction solution was stirred at room temperature for 18 hours. The mixture was poured over ice-cold saturated ammonium chloride and extracted into 25 mL of ethyl acetate. The layers were separated and the aqueous solution was washed with 20 mL of ethyl acetate. The combined ethyl acetate extracts were then washed successively with water and brine, dried over MgSO$_4$, filtered and evaporated to 191 mg of the crude material as a brown oil. Purification by flash chromatography, eluting with methylene chloride/methanol (25:1), afforded 77 mg (42% yield) of the product as a white powder. R$_1$: 0.44 (CH$_2$Cl$_2$/MeOH 10:1). $^1$H NMR (ppm, DMSO-$d_6$): 1.18 (t, 3 H), 3.7 (br s, 1 H), 4.25 (q, 2 H), 7.45 (2 H, ddd), 7.95 (2 H, dd). IR (cm$^{-1}$, KBr disk): 3434 (br w), 2714 (br m), 1737 (s), 1449 (m), 1411 (m), 1397 (m), 1303 (w), 1256 (m), 1190 (m), 1091(m), 980 (m), 839 (w), 783 (w), 760 (m).

Example 19

Synthesis of 5-(Benzothiazol-2-ylamino)-[1,2,3]thiadiazole-4-carboxylic acid amide A solution of dimethylaluminum amide was prepared by first dissolving approximately 250 mg of ammonia gas in 30 mL of dry methylene chloride at 0° C. in a 100 mL round bottom flask. Trimethylaluminum was added dropwise via syringe. The syringe needle was prone to becoming blocked; therefore, a continuous dropwise addition was maintained. The solution was allowed to warm to room temperature. The evolution of gas ceased after 25 minutes of reaction time. The concentration of the resulting solution was approximately 0.4 M. The dimethylaluminum amide solution (0.65 mL of a 0.4 M solution, 0.20 mmol) was added to 5-(benzothiazol-2-ylamino)-[1,2,3]thiadiazole-4-carboxylic acid ethyl ester (40 mg, 0.13 mmol) which had previously been dissolved in 2 mL of dry methylene chloride in a 25 mL flask. The reaction solution was then heated to reflux for 1 hour at which point and additional 2.4 mL of the dimethylaluminium amide solution was added. Refluxing of the solution was continued for an additional 24 hours at which point the reaction appeared more than 50% complete by TLC. The reaction solution was cooled to 0° C. and a solution of 5% HCl was added dropwise. The solution was allowed to warm to room temperature at which point effervescence occurred. The resulting solution was washed twice with ethyl acetate (30 mL). The organic layer was then washed successively with water and brine, dried over $MgSO_4$, filtered and evaporated to a pale yellow powder. The crude material was dissolved in methanol and evaporated onto silica gel which was then loaded on the top of a silica gel flash chromatography column. The column was eluted with methylene chloride/methanol (5:1) to afford the product in the amount of 5 mg (14% yield) as a tan solid. R: 0.21 ($CH_2Cl_2$.MeOH=10:1). $^1$H NMR (ppm, DMSO-$d_6$): 7.35 (br s, 1 H), 7.38 (2 H, ddd), 7.76 (br s, 1 H), 7.93 (2 H, dd). IR ($cm^{-1}$, KBr disk): 3339 (br s), 3181 (br s), 2730 (br m), 2615 (m), 1661 (s), 1595 (m), 1506 (m), 1455 (m), 1426 (m), 1405 (s), 1346 (w), 1313 (w), 1093 (m), 1025 (w), 1010 (w), 984 (m), 756 (m), 723 (m), 689 (w).

Example 20

Synthesis of 5-(3,5-dichlorophenylamino)-[1,2,3] thiadiazole-4-carboxylic acid amide Under anhydrous conditions, acetoacetamide (0.5 g, 5.0 mmol) was dissolved in 99% anhydrous THF resulting in a 0.5 M solution. To this mixture was added t-BuOK in THF 1 M solution (5 mL, 5.0 mmol) was added in a single portion, resulting in the immediate formation of a white precipitate. The reaction vessel was then submerged in an ultrasonic in order to break up the precipitate and form a uniform heterogeneous solution. 3,5-Dichlorophenyl isothiocyanate (1.0 g, 5.0 mmol) was then added in drop wise to this solution, resulting in a yellow heterogeneous solution, which was stirred for 1 hour at room temperature. The reaction was monitored with tlc developed in 5% methanol 95% methylene chloride. The 5-(3,5-dichlorophenyl-thiocarbamoyl)-3-oxo-butyramide was then isolated via filtration and dried under high vacuum to yield a yellow precipitate (1.5 g, 99%). The 5-(3,5-dichlorophenyl-thiocarbamoyl)-3-oxo-butyramide (1.4 g, 4.6 mmol) was then dissolved in water and basified with 2 N KOH (pH=13–14) while stirring. The solution was stirred at room temperature for 30 minutes, and then quenched with 1.56 N hydrochloric acid (pH=2–3), yielding the yellow powder, 5-(3,5-dichlorophenylthiocarbamoyl)acetamide, isolated by filtration and dried under high vacuum (0.82 g, 68%). The 5-(3,5-dichloro-phenylthiocarbamoyl)acetamide (0.5 g, 1.9 mmol) was then dissolved in minimal amounts of ethanol and heated to 45° C. while stirring generating a transparent yellow solution. To this solution was added triethylamine (265 µL, 1.9 mmol) followed by an excess of p-tosyl azide. A light yellow precipitate then formed approximately 10 minutes later and was isolated then dried (0.41 g, 75%). MS (m/z, ES—): 290 ($M^+$).

Example 21

Additional compounds prepared by the method of Example 20

The following compounds were prepared following the method described in Example 20:

5-(4-Fluorophenylamino)-[1,2,3]thiadiazole-4-carboxylic acid amide: To a solution of acetoacetamide (0.5 g, 5.0 mmol) and t-BuOK in THF was added 4-fluoro-phenyl isothiocyanate (0.95 g, 4.0 mmol), after the isolation the wet powder transferred to a RBF using ethanol to facilitate the transfer. This was then dried under vacuum distillation, resulting in a transparent glassy substance. A developed tlc indicated an impure product (several spots), however the deprotection was carried out with, resulting in a yellow 5-(4-fluorophenylthiocarbamoyl)-3-oxo-butyramide (1.0 g). This intermediate (0.50 g, 2.4 mmol) was reacted with an excess amount of p-tosyl azide in the presence of triethylamine (330 µL, 2.4 mmol), the yellow powder was filtered and dried (0.29 g, 60%). $^1$H NMR (ppm, DMSO-$d_6$, 200 MHz): 7.2 (m, 4 H), 7.8 (s, 1 H), 8.2 (s, 1 H), 10.8 (s, 1 H).

5-(2-Fluorophenylamino)-[1,2,3[thiadiazole-4-carboxylic acid amide: To a solution of acetoacetamide (1.4 g, 13.8 mmol) and t-BuOK in THF was added 2-fluorophenyl isothiocyanate (2.1 g, 13.8 mmol) resulting in a yellow 5-(2-fluorophenyl-thiocarbamoyl)-3-oxo-butyramide (3.2 g, 91%). The 5-(2-fluorophenylthiocarbamoyl)-3oxo-butyramide (1.0 g, 4.0 mmol) was then deprotected resulting in a yellow plate crystals 5-(2-fluorophenylthiocarbamoyl) acetamide (0.85 g, 37%). This intermediate (0.20 g, 0.94 mmol) was reacted with an excess amount of p-tosyl azide in the presence of triethylamine (130 µL, 0.94 mmol), the light yellow powder was filtered and dried (51 mg, 23%). MS (m/z, ES—) 239 ($M^+$). $^1$H NMR (ppm, DMSO-$d_6$, 200 MHz): 7.3 (m, 4 H), 8.0 (s, 1 H), 8.4 (s, 1 H), 11.3 (s, 1 H).

5-(2,4-Dichlorophenylamino)-[1,2,3]thiadiazole-4-carboxylic acid amide: To a solution of acetoacetamide (0.5 g, 5.0 mmol) and t-BuOK in THF was added 2,4-dichlorophenyl isothiocyanate (1.1 g, 5.0 mmol) resulting in light yellow 5-(2,4-dichloro-phenylthiocarbamoyl)-3-oxo-butyramide (1.5 g, 99%). The 5-(2,4-dichlorophenyl-thiocarbamoyl)-3-oxo-butyramide (1.0 g, 3.4 mmol) was then deprotected resulting in a yellow 5-(2,4-dichlorophenylthiocarbamoyl)acetamide (0.6 g, 67%). This intermediate (0.35 g, 1.3 mmol) was reacted with an excess amount of p-tosyl azide in the presence of triethylamine (190 µL, 1.3 mmol), the yellow powder was filtered and dried (0.27 g, 71%). MS (ES—) m/z 291 $[M]^+$; $^1$H NMR (DMSO-$d_6$, 200 MHz) δ7.4 (d, 1 H), 7.6 (d, 1 H), 7.8 (s, 1 H), 8.0 (s, 1 H), 8.5 (s, 1 H), 11.7 (s, 1 H).

5-(4-Methylphenylamino)-1,2,3]thiadiazole-4-carboxylic acid amide: To a solution of acetoacetamide (0.5 g, 5.0 mmol) and t-BuOK in THF was added 4-methyl-phenyl isothiocyanate (0.86 g, 5.0 mmol) resulting in a yellow 5-(4-methylphenyl-thiocarbamoyl)-3-oxo-butyramide (1.1 g, 90%). The 5-(4-methylphenylthiocarbamoyl)-3-oxo-butyramide (1.0 g, 2.9 mmol) was then deprotected resulting in a yellow 5-(4-methylphenylthiocarbamoyl)acetamide (0.27 g, 33%). This intermediate (0.20 g, 0.96 mmol) was reacted with an excess amount of p-tosyl azide in the presence of triethylamine (135 µL, 0.96 mmol), the yellow powder was filtered and dried (93 mg, 41%). MS (m/z, ES—) 235 ($M^+$). $^1$H NMR (ppm, DMSO-$d_6$, 200 MHz): 2.3 (s, 3 H), 7.3 (m, 4 H), 7.8 (s, 1 H), 8.3 (s, 1 H), 10.9 (s, 1 H).

5-(4-Ethoxyphenylamino)-[1,2,3]thiadiazole-4-carboxylic acid amide: To a solution of acetoacetamide (0.5 g, 5.0 mmol) and t-BuOK in THF was added 4-ethoxyphenyl isothiocyanate (0.95 g, 5.3 mmol) resulting in a yellow 5-(4-ethoxyphenyl-thiocarbamoyl)-3-oxo-butyramide (1.2 g, 84%). The 5-(4-ethoxyphenylthiocarbamoyl)-3-oxo-butyramide (1.0 g, 3.6 mmol) was then deprotected resulting in a yellow 5-(4-ethoxyphenylthiocarbamoyl)acetamide (0.28 g, 33%). This intermediate (0.20 g, 0.84 mmol) was reacted with an excess amount of p-tosyl azide in the presence of triethylamine (120 μL, 0.84 mmol), the yellow powder was filtered and dried (60 mg, 27%). MS (m/z, ES—): 263 (M$^+$). $^1$H NMR (ppm, DMSO-d$_6$, 200 MHz): 1.3 (t, 3 H), 4.0 (q, 2 H), 7.0 (d, 2 H), 7.2 (d, 2 H), 7.8 (s, 1 H), 8.2 (s, 1 H), 10.6 (s, 1 H).

5-(4-Benzyloxyphenylamino)-[1,2,3]thiadiazole-4-carboxylic acid amide. To a solution of acetoacetamide (0.4 g, 4.0 mmol) and t-BuOK in THF was added 4-benzyloxyphenyl isothiocyanate (1.02 g, 4.0 mmol) resulting in a yellow 5-(4-benzyloxy-phenylthiocarbamoyl)-3-oxo-butyramide (1.2 g, 74%). The 5-(4-benzyloxyphenylthiocarbamoyl)-3-oxo-butyramide (1.0 g, 2.9 mmol) was then deprotected resulting in a yellow 5-(4-benzyloxyphenylthiocarbamoyl)acetamide (0.82 g, 93%). This intermediate (0.50 g, 1.7 mmol) was reacted with an excess amount of p-tosyl azide in the presence of triethylamine (235 μL, 1.67 mmol), the yellow powder was filtered and dried (25 mg, 4%). MS (m/z, ES—): 325 (M$^+$). $^1$H NMR (ppm, DMSO-d$_6$, 200 MHz): 5.2 (s, 2 H), 7.0–7.6 (m, 9 H), 7.8 (s, 1 H), 8.2 (s, 1 H), 10.6 (s, 1 H).

5-(4-Phenylazophenylamino)-[1,2,3]thiadiazole-4-carboxylic acid amide: To a solution of acetoacetamide (0.5 g, 5.0 mmol) and t-BuOK in THF was added 4-phenylazophenyl isothiocyanate (0.95 g, 4.0 mmol) resulting in a bright orange 5-(4-phenylazophenylthiocarbamoyl)-3-oxo-butyramide (1.1 g, 84%). The 5-(4-phenylazophenylthiocarbamoyl)-3-oxo-butyramide (1.0 g, 2.9 mmol) was then deprotected resulting in an orange 5-(4-phenylazophenylthiocarbamoyl)acetamide (0.49 g, 56%). This intermediate (0.30 g, 1.0 mmol) was reacted with an excess amount of p-tosyl azide in the presence of triethylamine (150 μL, 1.0 mmol), the bright orange powder was filtered and dried (0.14 g, 44%). MS (m/z, ES—): 323 (M$^+$). $^1$H NMR (ppm, DMSO-d$_6$, 200 MHz): 7.8 (m, 4 H), 8.0 (m, 6 H), 8.4 (s, 1 H), 11.4 (s, 1 H).

5-(4-Methylsulfanylphenylamino)-[1,2,3]thiadiazole-4-carboxylic acid amide: To a solution of acetoacetamide (0.5 g, 5.0 mmol) and t-BuOK in THF was added 4-methylsufanylphenyl isothiocyanate (0.95 g, 4.0 mmol) resulting in a yellow 5-(4-methylsufanylphenylthiocarbamoyl)-3-oxo-butyramide (1.1 g, 84%). The 5-(4-methylsufanylphenylthiocarbamoyl)-3-oxo-butyramide (1.0 g, 2.9 mmol) was then deprotected resulting in a yellow 5-(4-methylsufanylphenylthiocarbamoyl)acetamide (0.43 g, 51%). This intermediate (0.30 g, 1.3 mmol) was reacted with an excess amount of p-tosyl azide in the presence of triethylamine (180 μL, 1.3 mmol), the bright yellow powder was filtered and dried (35 mg, 11%). MS (m/z, ES—): 265 (M$^+$).

5-(2-Methylsulfanylphenylamino)-[1,2,3]thiadiazole-4-carboxylic acid amide: To a solution of acetoacetamide (0.5 g, 5.0 mmol) and t-BuOK in THF was added 2-methylsufanylphenyl isothiocyanate (0.95 g, 4.0 mmol) resulting in an off white 5-2-methylsufanylphenylthiocarbamoyl)-3-oxo-butyramide (1.4 g, 100%). The 5-(2-methylsufanylphenylthiocarbamoyl)-3-oxo-butyramide (1.0 g, 2.9 mmol) was then deprotected resulting in a bright yellow 5-(2-methylsufanylphenylthiocarbamoyl)-acetamide (0.5 g, 59%). This intermediate (0.30 g, 1.3 mmol) was reacted with an excess amount of p-tosyl azide in the presence of triethylamine (180 μL, 1.3 mmol), the white powder was filtered and dried (30 mg, 9%). MS (m/z, ES—): 265 (M$^+$).

5-(3-Methoxybiphenyl-4-ylamino)-[1,2,3]thiadiazole-4-carboxylic acid amide: To a solution of acetoacetamide (0.5 g, 5.0.mmol) and t-BuOK in THF was added 3-phenyl-2-methoxyphenyl isothiocyanate (1.19 g, 5.0 mmol) resulting in yellow 5-(4-methoxybiphenyl-3-ylamino)-3-oxo-butyramide (1.2 g, 68%). The 5-(4-methoxy-biphenyl-3-ylamino)-3-oxo-butyramide (1.1 g, 3.1 mmol) was then deprotected resulting in a yellow 5-(4-methoxybiphenyl-3-ylthiocarbamoyl)acetamide (0.82 g, 43%). This intermediate (0.5 g, 1.9 mmol). was reacted with an excess amount of p-tosyl azide in the presence of triethylamine (141 μL, 1.9 mmol), after the addition of minimal amounts DMF to form a homogeneous solution. The light yellow powder was filtered and dried (0.41 g, 47%). MS (m/z, ES—): 325 (M$^+$).

5-(4-Nitrophenylamino)-r[1,2,3]thiadiazole-4-carboxylic acid amide: To a solution of acetoacetamide (0.5 g, 5.0 mmol) and t-BuOK in THF was added 4-nitrophenyl isothiocyanate (0.89 g, 5.0 mmol) resulting in an orange 5-(4-nitrophenyl-thiocarbamoyl)-3-oxo-butyramide (1.2 g, 100%). The 5-(4-nitrophenylthiocarbamoyl)-3-oxo-butyramide (1.1 g, 3.1 mmol) was then deprotected resulting in a bright orange 5-(4-nitrophenylthiocarbamoyl)acetamide (0.39 g, 73%). This intermediate (0.5 g, 2.1 mmol) was reacted with an excess amount of p-tosyl azide in the presence of triethylamine (295 μL, 2.1 mmol), with the addition of minimal amounts DMF to form a homogeneous solution. The orange powder was filtered and dried (0.17 g, 30%). MS (m/z, ES—): 264 (M$^+$).

5-(4-Acetylphenylamino)-[1,2,3]thiadiazole-4-carboxylic acid amide: To a solution of acetoacetamide (0.5 g, 5.0 mmol) and t-BuOK in THF was added 4-acetylphenyl isothiocyanate (0.93 g, 5.0 mmol) resulting in bright yellow 5-(4-acetylphenyl-thiocarbamoyl)-3-oxo-butyramide (1.5 g, 100%). The 5-(4-acetylphenylthiocarbamoyl)-3-oxo-butyramide (1.4 g, 5.0 mmol) was then deprotected resulting in a bright yellow 5-(4-acetylphenylthiocarbamoyl)acetamide (0.27 g, 22%). This intermediate (0.21 g, 0.89 mmol) was reacted with an excess amount of p-tosyl azide in the presence of triethylamine (124 μL, 0.89 mmol), the yellow powder was filtered and dried (57 mg, 24%). MS (m/z, ES—): 261 (M$^+$).

5-(4-Trifluoromethylphenylamino)-[1,2,3]thiadiazole-4-carboxylic acid amide: To a solution of acetoacetamide (0.5 g, 5.0 mmol) and t-BuOK in THF was added 4-trifluoromethylphenyl isothiocyanate (1.04 g, 5.0 mmol) resulting in light yellow 5-(4-trifluoromethylphenylthiocarbamoyl)-3-oxo-butyramide (1.4 g, 94%). The 5-(4-trifluoromethylphenylthiocarbamoyl)-3-oxo-butyramide (1.3 g, 4.3 mmol) was then deprotected resulting in a light yellow 5-(4-trifluoromethylphenylthiocarbamoyl)-acetamide (0.7 g, 64%). This intermediate (0.5 g, 1.9 mmol) was reacted with an excess amount of p-tosyl azide in the presence of triethylamine (265 μL, 1.9 mmol), the white powder was filtered and dried (0.31 g, 56%). MS (m/z, ES—): 287 (M$^+$).

5-(2,5-Dimethoxyphenylamino)-[1,2,3]thiadiazole-4-carboxylic acid amide: To a solution of acetoacetamide (0.5 g, 5.0 mmol) and t-BuOK in THF was added 2,5-dimethoxyphenyl isothiocyanate (0.99 g, 5.0 mmol) resulting in yellow 5-(2,5-dimethoxy-phenylthiocarbamoyl)-3-oxo-butyramide (1.2 g, 78%). The 5-(2,5-dimethoxyphenyl-thiocarbamoyl)-3-oxo-butyramide (1.0 g, 3.5 mmol) was then deprotected resulting in a yellow 5-(2,5-dimethoxyphenylthiocarbamoyl)acetamide (0.46 g, 52%). This intermediate (0.4 g, 1.6 mmol) was reacted with an excess amount of p-tosyl azide in the presence of triethylamine (220 μL, 1.6 mmol), the off white powder was filtered and dried (0.1 g, 23%). MS (m/z, ES—): 279 (M$^+$).

5-(3,5-Dimethoxyphenylamino)-[1,2,3]thiadiazole-4-carboxylic acid amide: To a solution of acetoacetamide (0.5 g, 5.0 mmol) and t-BuOK in THF was added 3,5-dimethoxyphenyl isothiocyanate (0.99 g, 5.0 mmol) resulting in yellow 5-(3,5-dimethoxy-phenylthiocarbamoyl)-3-oxo-butyramide (1.1 g, 74%). The 5-(3,5-dimethoxyphenyl-thiocarbamoyl)-3-oxo-butyramide (1.0 g, 3.5 mmol) was then deprotected resulting in a yellow 5-(3,5-dimethoxyphenylthiocarbamoyl)acetamide (0.48 g, 56%). This intermediate (0.4 g, 1.6 mmol) was reacted with an excess amount of p-tosyl azide in the presence of triethylamine (220 μL, 1.6 mmol), followed by an excess amount of tosyl azide, the off white powder was filtered and dried (65 mg, 15%). MS (m/z, ES—): 279 ($M^+$).

5-(2,3-Dichlorophenylamino)-[1,2,3[thiadiazole-4-carboxylic acid amide: To a solution of acetoacetamide (0.5 g, 5.0 mmol) and t-BuOK in THF was added 2,3-dichlorophenyl isothiocyanate (1.0 g, 5.0 mmol) resulting in light yellow 5-(2,3-dichloro-phenylthiocarbamoyl)-3-oxo-butyramide (1.4 g, 90%). The 5-(2,3-dichlorophenyl-thiocarbamoyl)-3-oxo-butyramide (1.2 g, 4.0 mmol) was then deprotected resulting in a light yellow 5-(2,3-dichlorophenylthiocarbamoyl)acetamide (0.65 g, 62%). This intermediate (0.5 g, 1.9 mmol) was reacted with an excess amount of p-tosyl azide in the presence of triethylamine (265 μL, 1.9 mmol), the off white powder was filtered and dried (0.17 g, 31%). MS (m/z, ES—): 288 ($M^+$).

5-(3,4-Dichlorophenylamino)-[1,2,3]thiadiazole-4-carboxylic acid amide: To a solution of acetoacetamide (0.5 g, 5.0 mmol) and t-BuOK in THF was added 3,4-dichlorophenyl isothiocyanate (1.0 g, 5.0 mmol) resulting in light yellow 5-(3,4-dichloro-phenylthiocarbamoyl)-3-oxo-butyramide (1.0 g, 70%). The 5-(3,4-dichlorophenyl-thiocarbamoyl)-3-oxo-butyramide (1.0 g, 3.3 mmol) was then deprotected resulting in a light yellow 5-(3,4-dichlorophenylthiocarbamoyl)acetamide (0.63 g, 74%). This intermediate (0.5 g, 1.9 mmol) was reacted with an excess amount of p-tosyl azide in the presence of triethylamine (265 μL, 1.9 mmol), the off white powder was filtered and dried (0.12 g, 22%). MS (m/z, ES—): 288 ($M^+$).

5-(3,4-Dimethoxyphenylamino)-[1,2,3]thiadiazole-4-carboxylic acid amide: To a solution of acetoacetamide (0.5 g, 5.0 mmol) and t-BuOK in THF was added 3,4-dimethoxyphenyl isothiocyanate (0.97 g, 5.0 mmol) resulting in bright yellow 5-(3,4-dimethoxyphenylthiocarbamoyl)-3-oxo-butyramide (1.1 g, 76%). The 5-(3,4-dimethoxy-phenylthiocarbamoyl)-3-oxo-butyramide (1.0 g, 3.4 mmol) was then deprotected resulting in a bright yellow 5-(3,4-dimethoxyphenylthiocarbamoyl)acetamide (0.16 g, 18%). This intermediate (0.15 g, 0.5 mmol) was reacted with an excess amount of p-tosyl azide in the presence of triethylamine (80 μL, 0.5 mmol), the yellow powder was filtered and dried (0.11 g, 69%).

5-(3-Methoxtphenylamino)-[1,2,3]thiadiazole-4-carboxylic acid amide: To a solution of acetoacetamide (0.5 g, 5.0 mmol) and t-BuOK in THF was added 3-methoxyphenyl isothiocyanate (0.82 g, 5.0 mmol) resulting in a yellow 5-(3-methoxy-phenylthiocarbamoyl)-3-oxo-butyramide (1.0 g, 76%). The 5-(3-methoxyphenyl-thiocarbamoyl)-3-oxo-butyramide (0.96 g, 3.4 mmol) was then deprotected resulting in a bright yellow 5-(3-methoxyphenylthiocarbamoyl)acetamide (0.31 g, 38%). This intermediate (0.29 g, 1.28 mmol) was reacted with an excess amount of p-tosyl azide in the presence of triethylamine (180 μL, 1.28 mmol), the yellow powder was filtered and dried (50 mg, 16%).

5-(2-Methoxy-5-methylphenylamino)-1,2,3]thiadiazole-4-carboxylic acid amide: To a solution of acetoacetamide (0.5 g, 5.0 mmol) and t-BuOK in THF was added 2-methoxy-5-methylphenyl isothiocyanate (0.89 g, 5.0 mmol) resulting in a bright yellow 5-(2-methoxy-5-methylphenylthiocarbamoyl)-3-oxo-butyramide (0.84 g, 61%). The 5-(2-methoxy-5-methylphenylthiocarbamoyl)-3-oxo-butyramide (0.81 g, 2.9 mmol) was then deprotected resulting in a yellow 5-(2-methoxy-5-methylphenylthiocarbamoyl)-acetamide (0.23 g, 33%). This intermediate (0.21 g, 0.86 mmol) was reacted with an excess amount of p-tosyl azide in the presence of triethylamine (121 μL, 0.86 mmol), the yellow powder was filtered and dried (20 mg, 9%).

Example 22

Assessment of Effects on Cell Viability

Anti-tumour efficacy and dose response in allograft and xenograft models. Cell lines were selected from an in vitro assay based on ILK expression, and growth curves characterized in vivo. Preliminary tests were performed with the Lewis Lung cell line in a murine allograft tumor model. In parallel, human xenograft tumor lines were characterized.

Cells were inoculated subcutaneously in the rear flank of mice, and the test compound was administered i.p. daily. Tumors were measured and the size calculated, with the objective being a decrease in tumor growth compared to the controls.

The results demonstrated that KP-15807 succeeded in reducing tumor growth compared to control.

From the foregoing it will be appreciated that, although specific embodiments of the invention have been described herein for purposes of illustration, various modifications may be made without deviating from the spirit and scope of the invention. Accordingly, the invention is not limited except as by the appended claims.

All publications mentioned herein are incorporated herein by reference for the purpose of describing and disclosing, for example, the compounds and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. A compound of the formula

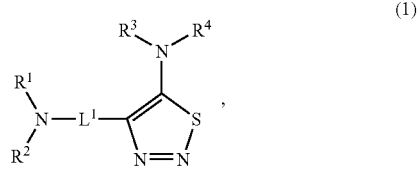

stereoisomers, pharmaceutically acceptable solvates, or pharmaceutically acceptable salts thereof, wherein $R^1$ and $R^2$ are the same or different and independently hydrogen, aryl, heteroalkyl or —$COCH_3$, wherein the heteroalkyl comprises 1–5 heteroatoms selected from nitrogen and oxygen, or $R^1$ and $R^2$ may together form a heterocyclic structure including the nitrogen to which they are both attached, $R^3$ is hydrogen or alkyl;

$R^4$ is aryl; and

L¹ is alkylene or heteroalkylene, wherein the heteroalkylene comprises 1–5 heteroatoms selected from nitrogen and oxygen.

2. A pharmaceutical composition comprising a compound of the formula (1) and a pharmaceutically acceptable carrier, diluent or excipient,

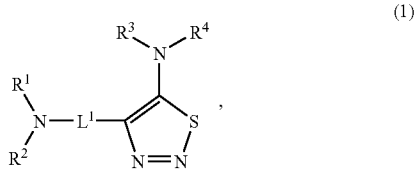

stereoisomers, pharmaceutically acceptable solvates, or pharmaceutically acceptable salts thereof, wherein $R^1$ and $R^2$ are the same or different and independently hydrogen, aryl, heteroalkyl or —COCH$_3$, wherein the heteroalkyl comprises 1–5 heteroatoms selected from nitrogen and oxygen, or $R^1$ and $R^2$ may together form a heterocyclic structure including the nitrogen to which they are both attached, $R^3$ is hydrogen or alkyl;

$R^4$ is aryl; and

L¹ is alkylene or heteroalkylene, wherein the heteroalkylene comprises 1–5 heteroatoms selected from nitrogen and oxygen.

3. The compound of claim 1 wherein L¹ is -CH$_2$—, —C(=O)—, —C(=O)NH—, —C(=O)NH-alkylene- or —C(O)—NH—C(=NH)—.

4. The compound of claim 3 wherein $R^1$ is hydrogen and $R^2$ is hydrogen, aryl, heteroalkyl or —COCH$_3$.

5. The compound of claim 3 wherein $R^1$ and $R^2$ together with the nitrogen they are attached form a morpholine.

6. The compound of claim 5 wherein L¹ is —C(=O)NH—.

7. The compound of claim 5 wherein L¹ is —C(=O)NH-ethylene-.

8. The composition of claim 2 wherein L¹ is —CH$_2$—, —C(=O)—, —C(=O)NH—, —C(=O)NH-alkylene- or —C(O)—NH—C(=NH)—.

9. The composition of claim 8 wherein $R^1$ is hydrogen and $R^2$ is hydrogen, aryl, heteroalkyl or —COCH$_3$.

10. The composition of claim 8 wherein $R^1$ and $R^2$ together with the nitrogen they are attached form a morpholine.

11. The composition of claim 10 wherein L¹ is —C(=O)NH—.

12. The composition of claim 10 wherein L¹ is —C(=O)NH-ethylene-.

* * * * *